US008010368B2

(12) United States Patent
Yamaki

(10) Patent No.: US 8,010,368 B2
(45) Date of Patent: Aug. 30, 2011

(54) SURGICAL SYSTEM CONTROLLING APPARATUS AND SURGICAL SYSTEM CONTROLLING METHOD

(75) Inventor: Masahide Yamaki, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 930 days.

(21) Appl. No.: 11/725,246

(22) Filed: Mar. 19, 2007

(65) Prior Publication Data

US 2007/0219806 A1    Sep. 20, 2007

(51) Int. Cl.
*G10L 13/00*  (2006.01)
*G10L 15/00*  (2006.01)
*A61B 1/00*   (2006.01)

(52) U.S. Cl. ........ 704/275; 600/101; 600/118; 704/231; 704/258

(58) Field of Classification Search .................... 704/275
See application file for complete search history.

(56) References Cited

U.S. PATENT DOCUMENTS

| 5,345,538 | A  | * | 9/1994 | Narayannan et al. | 704/275 |
| 6,278,975 | B1 | * | 8/2001 | Brant et al. | 704/275 |
| 7,286,992 | B2 | * | 10/2007 | Sander et al. | 704/275 |
| 2003/0225751 | A1 | * | 12/2003 | Kim | 707/3 |
| 2005/0256370 | A1 | * | 11/2005 | Fujita | 600/101 |
| 2006/0114175 | A1 | * | 6/2006 | Boukhny | 345/24 |
| 2008/0021711 | A1 | * | 1/2008 | Claus et al. | 704/275 |

FOREIGN PATENT DOCUMENTS

| JP | 10-133849 | 5/1998 |
| JP | 2000-005158 A | 1/2000 |
| JP | 2001-312297 A | 11/2001 |
| JP | 2002-247670 A | 8/2002 |
| JP | 2003-005777 | 1/2003 |
| JP | 2003-029778 | 1/2003 |
| JP | 2004-267634 | 9/2004 |
| JP | 2004-275360 | 10/2004 |
| JP | 2005-090838 | 4/2005 |
| JP | 2005-157166 | 6/2005 |

OTHER PUBLICATIONS

Japanese Office Action dated Sep. 28, 2010.

* cited by examiner

*Primary Examiner* — Justin W Rider
(74) *Attorney, Agent, or Firm* — Scully, Scott, Murphy & Presser, PC

(57) ABSTRACT

In this invention, a voice recognition engine 110 outputs to a controlling section 103 a matching state of a voice input signal as an error code. Then, the controlling section 103 determines the matching state based on the error code in the error determination section 105 and outputs to a voice synthesizing engine 113 guidance data according to the matching state based on a timing control by a guidance timing controlling section 107. According to such a configuration, this invention improves operability by voice operation, while reducing a risk of erroneous recognition by maintaining a predetermined matching rate.

28 Claims, 24 Drawing Sheets

| FIRST HIERARCHICAL LANGUAGE |
|---|
| SYSTEM AUTOMATIC SETTING |
| GAS INSUFFLATOR INSUFFLATION |
| GAS INSUFFLATOR PRESSURE SETTING |
| GAS INSUFFLATOR MODE |
| ELECTROCAUTERY KNIFE OUTPUT SETTING |
| WHITE BALANCE |
| CAMERA BRIGHTNESS ADJUSTMENT |
| VTR RECORDING |
| ⋮ |

FIG.31

ERROR GUIDANCE

| ERROR CODE | GUIDANCE AS TO CAUSE OF ERROR | GUIDANCE AS TO CONTENTS TO BE IMPROVED |
|---|---|---|
| 01 | VOICE INPUT LEVEL IS INSUFFICIENT | SPEAK LOUDER |
| 02 | PLURAL RECOGNITION RESULTS EXTRACTED | FOLLOWING COMMANDS RECOGNIZED<br>GAS INSUFFLATOR INSUFFLATION<br>GAS INSUFFLATOR PRESSURE SETTING<br>GAS INSUFFLATOR MODE<br>PRONOUNCE AGAIN |
| 03 | PART OF UTTERED PHRASES INCOGNIZABLE | @@ PART OF "GAS INSUFFLATOR @@" INCOGNIZABLE<br>WHAT IS @@ PART? (NOTE) |
| 04 | RECOGNIZED, BUT MATCHING RATE IS NOT HIGH | RECOGNIZED AS "GAS INSUFFLATOR INSUFFLATION"<br>YES OR NO? |
| 05 | RECOGNIZED UNREGISTERED PHRASES | UTTERED COMMAND IS UNRECOGNIZED |

(NOTE) @@ IS BEEP SOUND

FIG.35

| OCCURRED EVENT | GUIDANCE |
|---|---|
| SYSTEM START-UP | @ ○○ (HOUR) ×× (MINUTE) START OPERATION |
| REACH SET VALUE OF ABDOMINAL CAVITY PRESSURE | @ABDOMINAL CAVITY PRESSURE REACHED SET VALUE |
| OUTPUT TIME PERIOD ERROR OCCUR | @CONTINUOUS OUTPUT TIME PERIOD OF ELECTROCAUTERY KNIFE EXCEEDS △△ SECONDS |
| ABDOMINAL CAVITY PRESSURIZATION OCCUR | @ABDOMINAL CAVITY PRESSURIZATION OCCURRED |
| TUBE CLOGGING OCCUR | @TUBE CLOGGING OCCURRED |

(NOTE) @ IS BEEP SOUND

US 8,010,368 B2

SURGICAL SYSTEM CONTROLLING APPARATUS AND SURGICAL SYSTEM CONTROLLING METHOD

BACKGROUND OF THE INVENTION

1. Field of the Invention

The present invention relates to a surgical system controlling apparatus and a surgical system controlling method, and more particularly to a surgical system controlling apparatus including a characteristic voice processing unit for operating medical instruments with voice and a method for controlling the surgical system.

2. Description of the Related Art

In recent years, an endoscopic surgical operation and the like using an endoscope apparatus are performed at a medical site. In the endoscopic surgical operation, it is possible to perform various kinds of treatments, while observing with an endoscope by adding a plurality of surgical instruments to the endoscope apparatus. The plurality of surgical instruments are, for example, a gas insufflator used for inflating inside of an abdominal cavity, a treatment apparatus for therapeutic procedure, and a high-frequency cauterizing apparatus for resecting or coagulating a living tissue.

Furthermore, an endoscopic surgical system provided with the plurality of various kinds of instruments, which is used for performing an endoscopic surgical operation, is capable of operating and controlling a plurality of apparatuses.

The endoscopic surgical system includes, for the purpose of improving an operatability of the system, a display panel such as a liquid crystal panel, as a display section for an operator to confirm setting states of various instruments in a sterilized area, a remote operation apparatus such as a remote controller, as a remote operation section operated by the operator in the sterilized area to change functions and setting values of the various instruments, and in addition, a centralized operation panel provided on a touch panel with operation switches of the respective instruments, which is operated in a non-sterilized area by an assistant such as a nurse or the like according to instruction by the operator to change functions and setting values of the various kinds of instruments, a microphone for operating the various kinds of instruments with voice, and the like.

In the conventional endoscopic surgical system, when operating various kinds of instruments with voice, the operator is required to hierarchically and intentionally issue commands for operating the instruments. Consequently, the system is not user-friendly in performing a therapeutic procedure.

Therefore, for example, Japanese Unexamined Patent Application Publication No. 2003-5777 discloses an endoscopic surgical system capable of controlling a target instrument only by voice-inputting a state of the instrument using conversational phrases.

SUMMARY OF THE INVENTION

A surgical system controlling method according to the present invention, comprises a voice information inputting step in which operation state voice information related to operation state of a surgical instrument to be controlled is inputted; a voice recognition processing step in which the operation state voice information is recognized based on of operation state standard voice data; a guidance data storing step in which at least guidance data corresponding to a recognition state in the voice recognition processing step is stored; and a guidance voice generating step in which voice data based on the guidance data is generated, wherein the operation state voice information is hierarchically recognized in the voice recognition processing step, and voice data based on the guidance data is generated for each piece of the operation state voice information hierarchically recognized in the voice recognition processing step.

A surgical system controlling apparatus according to the present invention, comprises: a voice information inputting section for inputting operation state voice information related to an operation state of a surgical instrument to be controlled; a voice recognition processing section for recognizing the operation state voice information based on operation state standard voice data; a guidance data storing section for storing at least guidance data according to a recognition state in the voice recognition processing section; and a guidance voice generating section for generating voice data based on the guidance data, wherein, when a matching rate of either first operation state voice information or second operation state voice information with respect to the operation state standard voice data is equal to or lower than a predetermined first value, the voice recognition processing section judges that the operation state voice information cannot be hierarchically recognized; and when the voice recognition processing section judges that the operation state voice information cannot be hierarchically recognized, the guidance voice generating section generates voice data based on guidance as to causes of error and guidance as to contents to be improved which are stored in the guidance data storing section and allows the generated voice data to be outputted.

A surgical system controlling method according to the present invention, comprises: a voice information inputting step in which operation state voice information related to an operation state of a surgical instrument to be controlled is inputted; a voice recognition processing step in which the operation state voice information is recognized based on operation state standard voice data; a guidance data storing step in which at least guidance data according to a recognition state in the voice recognition processing step is stored; and a guidance voice generating step in which voice data based on the guidance data is generated, wherein, when a matching rate of either first operation state voice information or second operation state voice information with respect to the operation state standard voice data is equal to or lower than a predetermined first value, it is judged that the operation state voice information including the first operation state voice information and the second operation state voice information cannot be hierarchically recognized in the voice recognition processing step, and when it is judged that the operation state voice information cannot be hierarchically recognized in the voice recognition processing step, voice data based on guidance as to causes of error and guidance as to contents to be improved which are stored in the guidance data storing step is generated and allowed to be outputted in the guidance voice generating step.

The above and other objects, features and advantages of the present invention will become more clearly understood from the following description.

BRIEF DESCRIPTION OF THE DRAWINGS

FIGS. 1 to 35 relate to a first embodiment of the present invention; in which

FIG. 1 is a configuration diagram showing a whole configuration of an endoscopic surgical system;

FIG. 2 is a block diagram showing a connecting relation of each of instruments in the endoscopic surgical system of FIG. 1;

FIG. 3 is a block diagram showing a configuration of a system controller of FIG. 2;

FIG. 4 is a block diagram showing a configuration of a modification example of the system controller of FIG. 2;

FIG. 5 shows a configuration of a language database of FIG. 3;

FIG. 6 shows a first hierarchical language stored in a first hierarchical language database of FIG. 5;

FIG. 7 shows a second hierarchical language stored in a second hierarchical language database of FIG. 5;

FIG. 8 is a flowchart showing a flow of voice processing by a system controller of FIG. 3;

FIG. 9 is a first descriptive diagram describing the voice processing of FIG. 8;

FIG. 10 is a second descriptive diagram describing the voice processing of FIG. 8;

FIG. 11 is a third descriptive diagram describing the voice processing of FIG. 8;

FIG. 12 is a fourth descriptive diagram describing the voice processing of FIG. 8;

FIG. 13 is a fifth descriptive diagram describing the voice processing of FIG. 8;

FIG. 14 is a sixth descriptive diagram describing the voice processing of FIG. 8;

FIG. 15 is a seventh descriptive diagram describing the voice processing of FIG. 8;

FIG. 16 is an eighth descriptive diagram describing the voice processing of FIG. 8;

FIG. 17 is a ninth descriptive diagram describing the voice processing of FIG. 8;

FIG. 18 is a tenth descriptive diagram describing the voice processing of FIG. 8;

FIG. 19 is an eleventh descriptive diagram describing the voice processing of FIG. 8;

FIG. 20 is a twelfth descriptive diagram describing the voice processing of FIG. 8;

FIG. 21 is a thirteenth descriptive diagram describing the voice processing of FIG. 8;

FIG. 22 is a fourteenth descriptive diagram describing the voice processing of FIG. 8;

FIG. 23 is a fifteenth descriptive diagram describing the voice processing of FIG. 8;

FIG. 24 is a first flowchart showing a flow of a voice recognition processing of FIG. 8;

FIG. 25 is a second flowchart showing the flow of the voice recognition processing of FIG. 8;

FIG. 26 is a first diagram describing a flow of data in the language database of FIG. 5 in the voice recognition processing;

FIG. 27 is a second diagram describing a flow of data in the language database of FIG. 5 in the voice recognition processing;

FIG. 28 is a third diagram describing a flow of data in the language database of FIG. 5 in the voice recognition processing;

FIG. 29 is a fourth diagram describing a flow of data in the language database of FIG. 5 in the voice recognition processing;

FIG. 30 is a fifth diagram describing a flow of data in the language database of FIG. 5 in the voice recognition processing;

FIG. 31 shows error guidance provided in the processing of FIG. 8;

FIG. 32 is a flowchart showing a flow of processing by the system controller of FIG. 2 to an event occurred in the system;

FIG. 33 is a first diagram showing a transition of a control state of the system controller in the processing of FIG. 32;

FIG. 34 is a second diagram showing a transition of a control state of the system controller in the processing of FIG. 32; and FIG. 35 shows guidance in the processing of FIG. 32.

DETAILED DESCRIPTION OF THE PREFERRED EMBODIMENTS

First Embodiment

Figure 1:
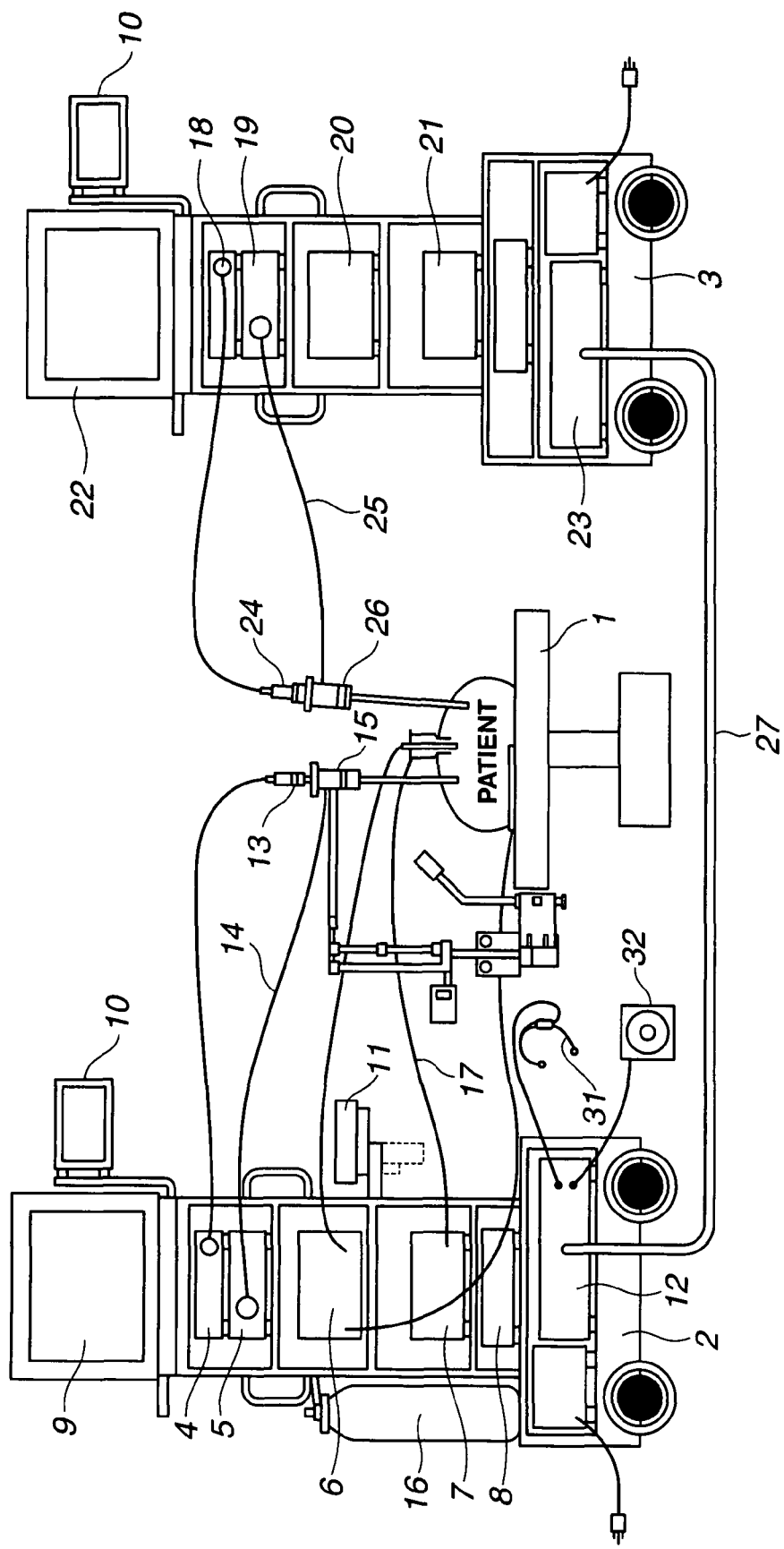
Figure 2:
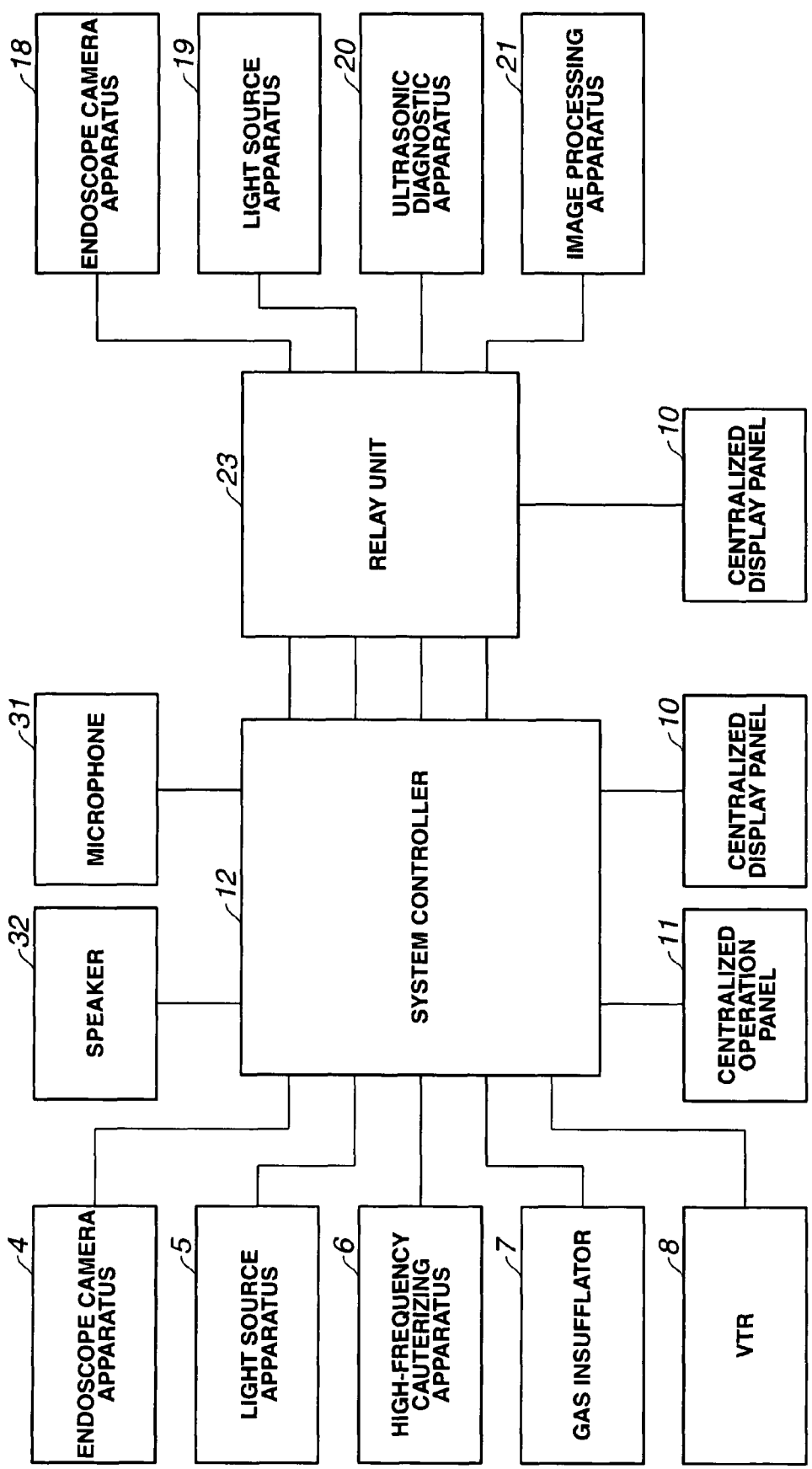

As shown in FIGS. 1 and 2, an endoscopic surgical system of the present embodiment includes a first cart 2 and a second cart 3 which are disposed on both sides of an operating table 1 on which a patient lies. The first cart 2 and the second cart 3 have mounted thereon a plurality of endoscope peripheral instruments, which are apparatuses to be controlled.

The first cart 2 has mounted thereon an endoscope camera apparatus 4, a light source apparatus 5, a high-frequency cauterizing apparatus (electrocautery knife) 6, a gas insufflator 7, a VTR 8, a first monitor 9, a centralized display panel 10, a centralized operation panel 11 to be remotely operated by a nurse and the like, and a system controller 12 which is a surgical system controlling apparatus.

The respective instruments are connected with the system controller 12 by a serial interface cable not shown, thereby enabling bi-directional communication.

In addition, the endoscope camera apparatus 4 and the light source apparatus 5 are connected with an endoscope camera head 13 and a light guide 14, respectively. The endoscope camera head 13 and the light guide 14 are respectively connected to an endoscope 15. The gas insufflator 7 is connected with a $CO_2$ tank 16. From an insufflation tube 17 extended from the gas insufflator 7 to a patient, $CO_2$ gas is supplied to an abdominal cavity of the patient.

On the other hand, the second cart 3 has mounted thereto an endoscope camera apparatus 18, a light source apparatus 19, an ultrasonic diagnostic apparatus 20, an image processing apparatus 21, a second monitor 22, a centralized display panel 10, and a relay unit 23.

The respective endoscope peripheral instruments are connected with the relay unit 23 by a serial interface cable not shown, thereby enabling bi-directional communication.

In addition, the endoscope camera 18 and the light source apparatus 19 are connected with an endoscope camera head 24 and a light guide 25, respectively. The endoscope camera head 24 and the light guide 25 are respectively connected to an endoscope 26.

Furthermore, the system controller 12 and the relay unit 23 are connected with each other by a system interface cable 27, thereby enabling bi-directional communication.

The centralized operation panel 11 is configured by a display section such as a liquid crystal display and a touch sensor integrally provided on the display section.

The centralized operation panel 11 has, in addition to a display function of displaying states of the respective apparatuses of the endoscopic surgical system of the present embodiment and displaying operation switches as a setting screen, an operation function by the operation switches by touching a predetermined area of the touch sensor.

The endoscopic surgical system is capable of performing operations equivalent to direct operations of the respective endoscope peripheral instruments via the system controller 12, using a touch panel (T.P) function configured by the display function and the operation function of the centralized operation panel 11.

In addition, to the system controller 12, a microphone 31 for voice inputting can be connected.

The system controller 12 recognizes the voice inputted from the microphone 31 by a voice processing section 12b (See FIG. 3) to be described later. Then, the system controller 12 outputs from a speaker 32 voice guidance corresponding to the recognized voice by means of the voice processing section 12b, thereby enabling control of each of the instruments by the voice guidance to be securely performed.

The microphone 31 is used as a remote operation section for centrally and remotely operating the peripheral instruments frequently used by an operator. The microphone 31 is used so that the operator himself/herself can freely set and operate the frequently used endoscope peripheral instruments with his/her voice while staying at a sterilized area.

Figure 3:
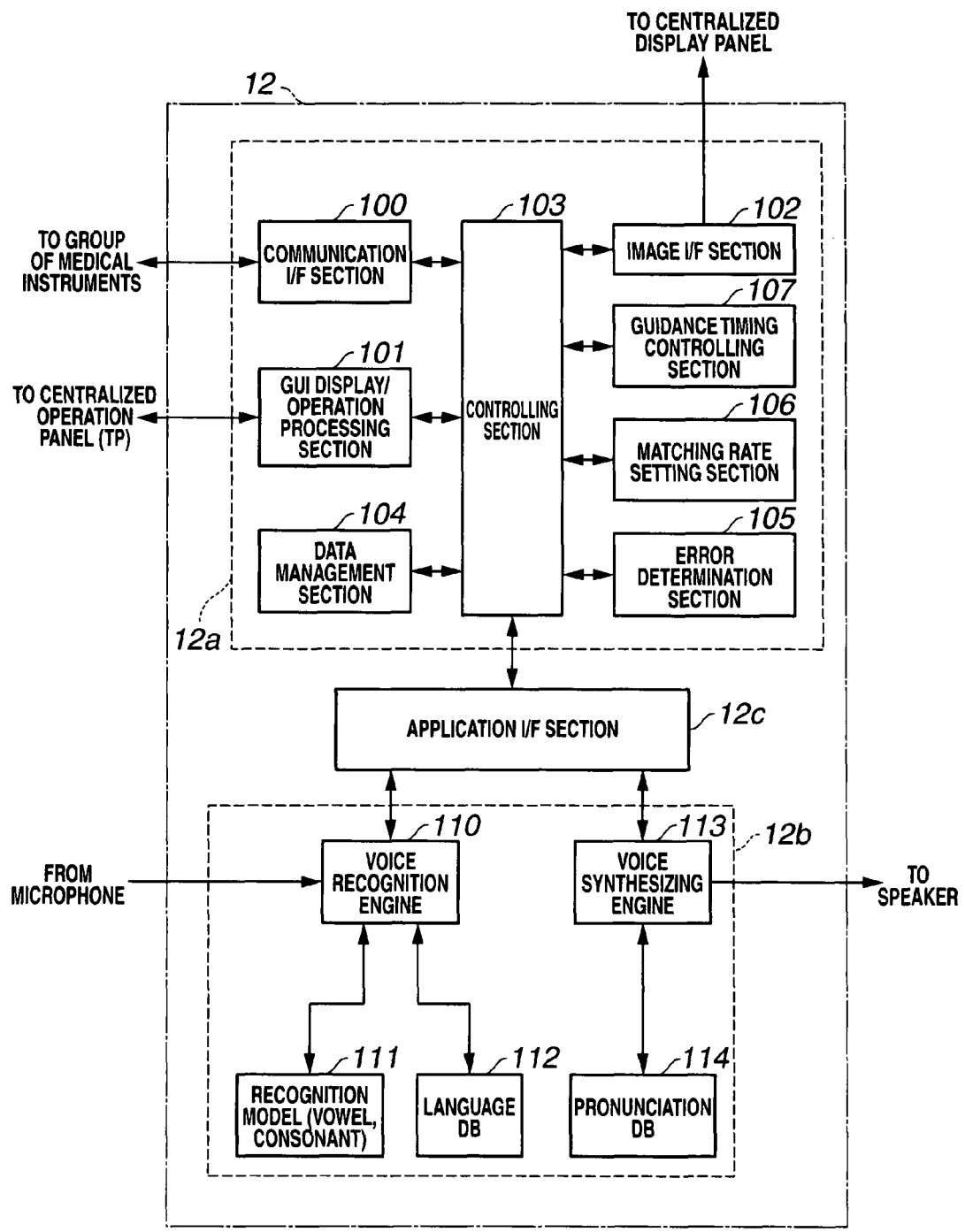

The system controller 12 includes a system controlling section 12a, a voice processing section 12b, and an application I/F section 12c, as shown in the function block diagram of FIG. 3. The system controller 12 sends and receives data between the system controlling section 12a and the voice processing section 12b via the application I/F section 12c.

The system controlling section 12a includes a communication I/F section 100, a GUI display/operation processing section 101, an image I/F section 102, and a controlling section 103.

The communication I/F section 100 serves as a communication interface with a group of medical instruments including the endoscope camera apparatus 4, the light source apparatus 5, the high-frequency cauterizing apparatus (electrocautery knife) 6, the gas insufflator 7, the VTR 8, and the relay unit 23.

The GUI display/operation processing section 101 serves as a touch panel interface with the centralized operation panel 11.

In addition, the image I/F section 102 serves as an interface for displaying a display image on the centralized display panel 10.

The controlling section 103 controls the respective sections, and controls the voice processing in the voice processing section 12b by using a data management section 104, an error determination section 105, a matching rate setting section 106, and a guidance timing controlling section 107.

The voice processing section 12b includes a voice recognition engine 110 which digitally converts a voice input signal from the microphone 31 to perform voice recognition processing, and a voice synthesizing engine 113 which converts guidance data from the controlling section 103 into a voice signal. Note that the guidance data is stored in the data management section 104.

The voice recognition engine 110 first digitally converts the voice input signal from the microphone 31. Then, the voice recognition engine 110, by using a recognition model 111 including vowels and consonants and a language database (DB) 112, extracts language matching with the voice input signal at a predetermined matching rate from the language stored in the language database (DB) 112. After that, the voice recognition engine 110 outputs the extracted language to the controlling section 103 via the application I/F section 12c, and the data management section 104 manages/stores the extracted language.

Furthermore, the voice synthesizing engine 113 outputs to the speaker 32, as a voice output signal by using voice data in a pronunciation DB 114, the guidance data to be outputted from the controlling section 103 via the application I/F section 12c according to a timing control by the guidance timing controlling section 107.

Figure 4:
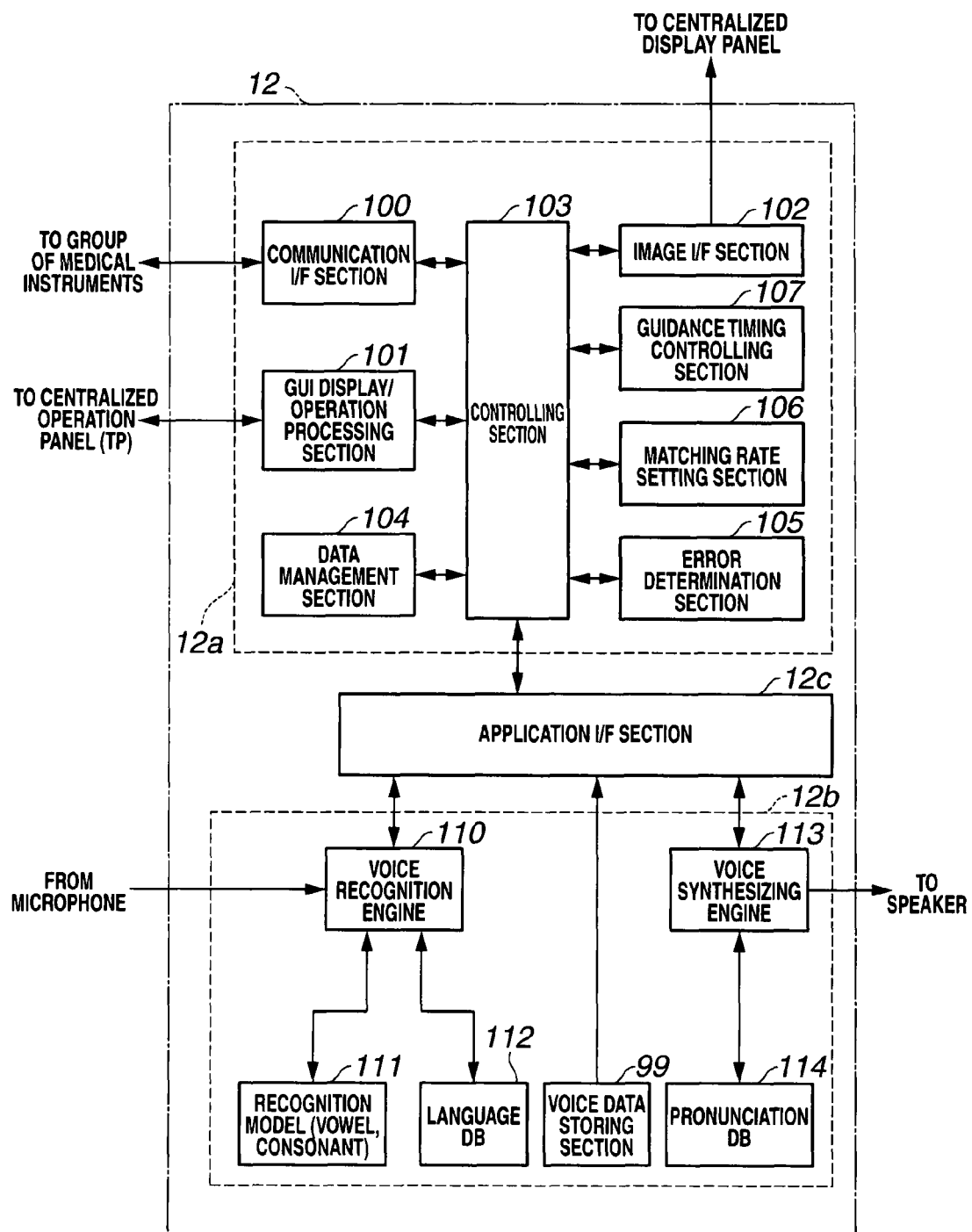

Though, in the present embodiment, the guidance is outputted from the voice synthesizing engine 113, the same effect can be obtained also in a case where recorded voice file (wav file and the like) is read out from a voice data storing section 99 to be outputted as a voice output signal to the speaker 32, as shown in FIG. 4.

The voice recognition engine 110 outputs to the controlling section 103 a matching state of the voice input signal as an error code to be described later. Then, the controlling section 103 determines the matching state in the error determination section 105 based on the error code, to output to the voice synthesizing engine 113 the guidance data corresponding to the matching state, according to the timing control by the guidance timing control section 107.

Figure 5:
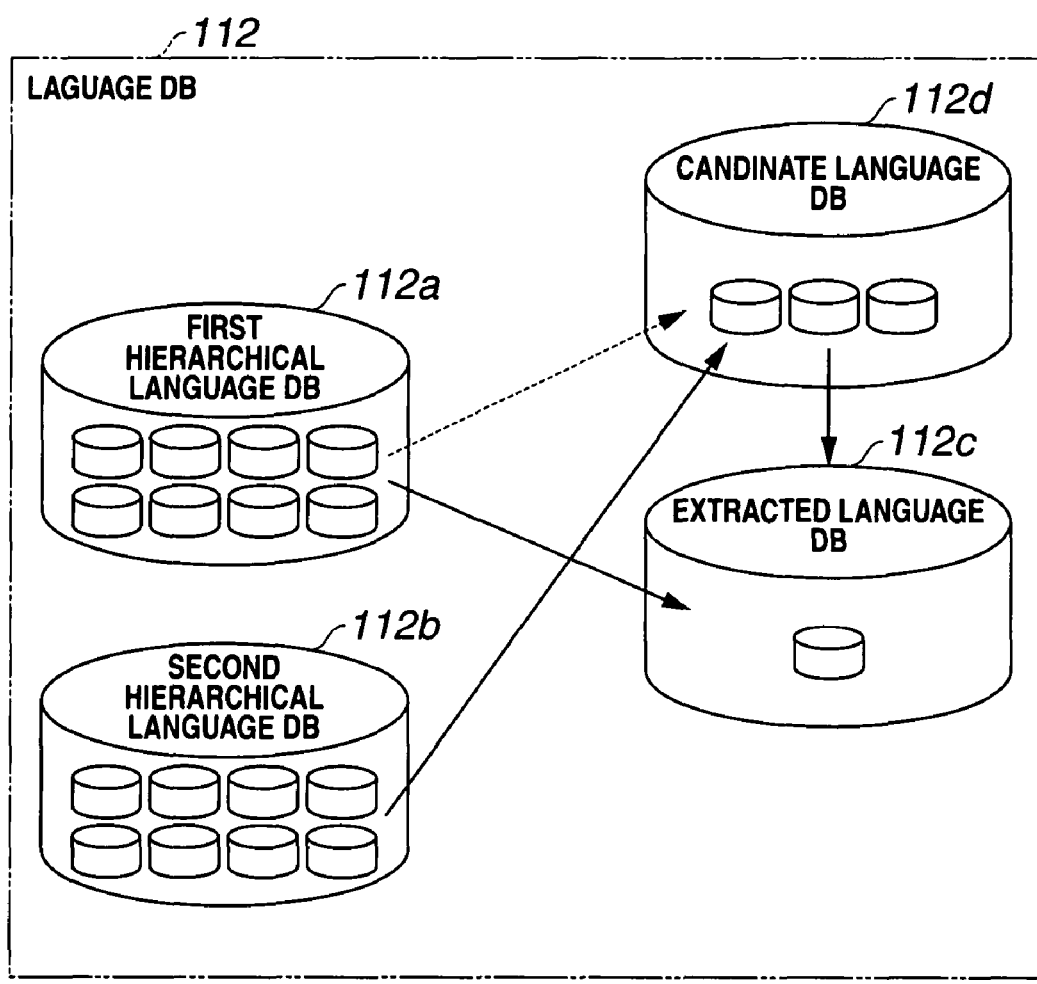

In the present embodiment, the voice input signal is hierarchically recognized and processed by the voice recognition engine 110. To this end, the language DB 112 is a database having a hierarchical structure including a first hierarchical language DB 112a and a second hierarchical language DB 112b, as shown in FIG. 5. The voice input signal of the first hierarchical language is inputted to be voice-recognized, and thereafter the language corresponding to the recognized signal is extracted from the first hierarchical language DB 112a to be stored in an extracted language DB 112c. The voice recognition engine 110 outputs the extracted language and the error code to the controlling section 103.

When the extraction of the first hierarchical language is finished, the language of the second hierarchical language associated with the extracted language of the first hierarchical language is stored in a candidate language DB 112d as a candidate language. Then, the voice input signal of the second hierarchical language is inputted to be voice-recognized, and thereafter the language corresponding to the signal is extracted from the candidate language DB 112d to be stored in the extracted language DB 112c. The voice recognition engine 110 outputs the extracted language and the error code to the controlling section 103.

Figures 6, 7:
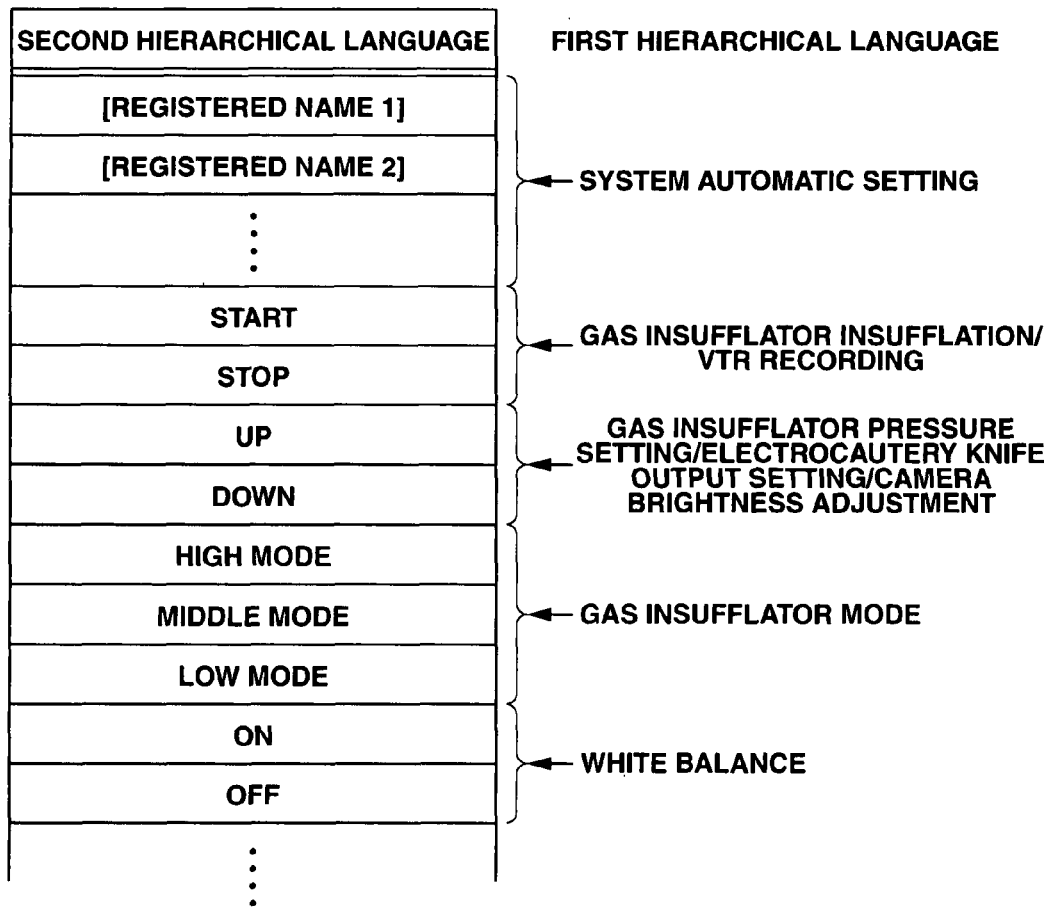

An example of the first hierarchical language and an example of the second hierarchical language are shown in FIG. 6 and FIG. 7, respectively. As shown in FIGS. 6 and 7, when the first hierarchical language is recognized as "system automatic setting", a plurality of registered names: "[registered name 1]", "[registered name 2]", . . . , for example, operators' names, which are registered in advance in association with "system automatic setting" are read out from the second hierarchical language DB 112b to be stored as the candidate language in the candidate language DB 112d.

Similarly, when the first hierarchical language is recognized as "gas insufflator insufflation", "start" and "stop" which are registered in advance in association with "gas insufflator insufflation" are read out from the second hierarchical language DB 112b to be stored as candidate language in the candidate language DB 112d.

The first hierarchical language includes, in addition to the above, "gas insufflator pressure setting", "gas insufflator mode", "electrocautery knife output setting", "white balance", "camera brightness adjustment", "VTR recording", and the like. In addition, the second hierarchical language includes, in addition to the above, "up", "down", "high mode", "middle mode", "low mode", and the like, which are associated with the first hierarchical language, as shown in FIG. 7.

In the present embodiment, when both of the first hierarchical language and the second hierarchical language are recognized, one command is determined. For example, when the first hierarchical language "gas insufflator insufflation" and the second hierarchical language "start" are recognized, a command "start gas insufflator insufflation" is determined.

Next, details of working of the present embodiment configured as such will be described.

Figure 8:
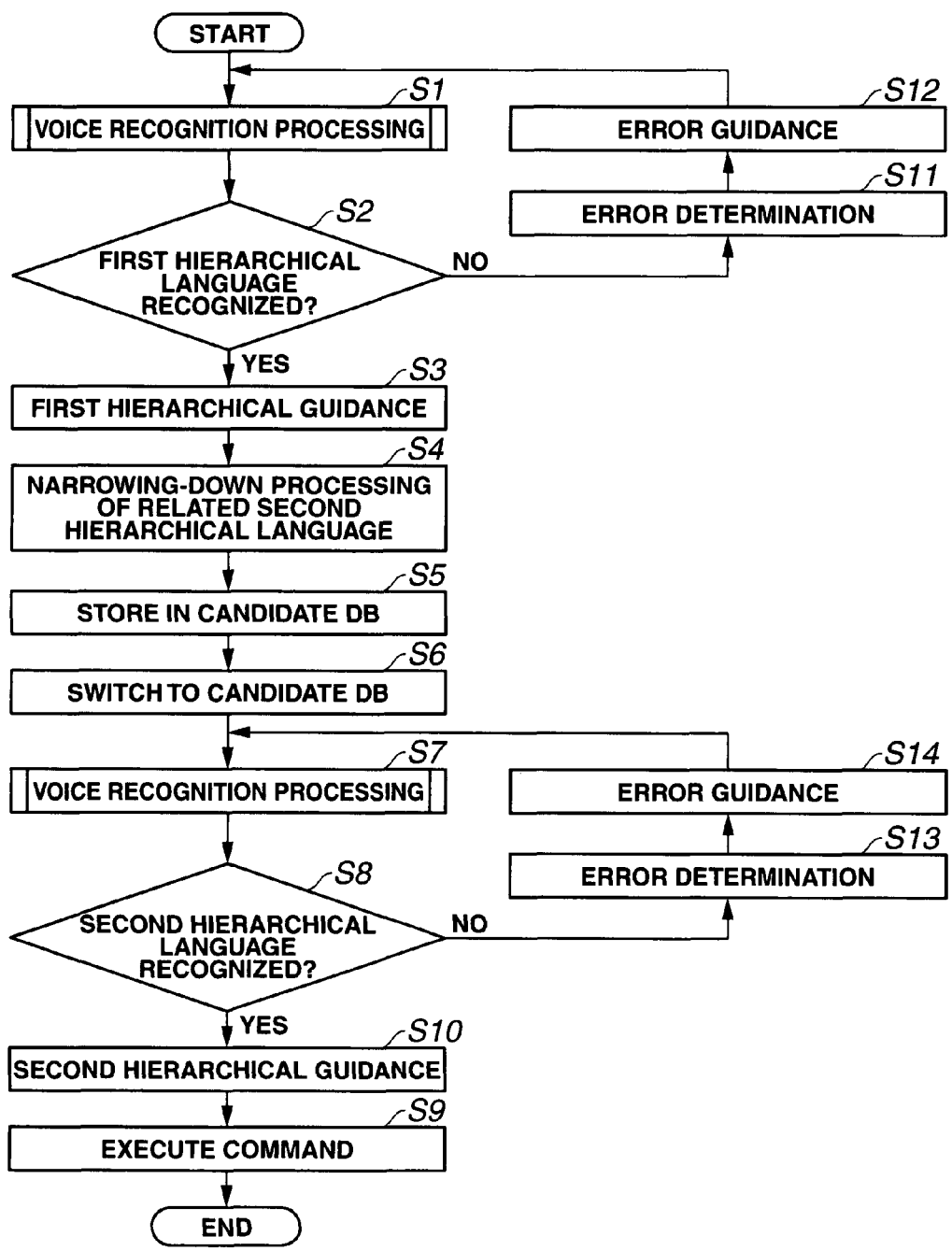

The system controller 12 sets the first hierarchical language DB 112a as a target database for voice recognition processing at default, and performs voice recognition processing by the voice recognition engine 110 on a voice command uttered by an operator by using the first hierarchical language DB 112a in Step S1, as shown in FIG. 8. Details of the voice recognition processing will be described later.

As a result of the voice recognition processing, the system controller 12 judges in Step S2 whether or not the voice command uttered by the operator is recognized as the first hierarchical language. When the command is recognized as the first hierarchical language, the system controller 12 causes the voice synthesizing engine 113 to utter the first hierarchical guidance corresponding to the first hierarchical language from the speaker 32 in Step S3.

Then, the system controller 12 narrows down the language of the second hierarchical language associated with the recognized first hierarchical language as the candidate language in Step S4, and stores the candidate language in the candidate language DB 112d in Step S5.

Subsequently, the system controller 12 switches the target database for the voice recognition processing in the voice recognition engine 110, from the first hierarchical language DB 112a to the candidate language DB 112d in Step S6. After that, in Step S7, similar voice recognition processing as that in Step S1 is performed, in the voice recognition engine 110 using the candidate language DB 112d, on the voice command uttered by the operator urged by the first hierarchical guidance within a predetermined interval time period (for example, three seconds).

As a result of the voice recognition processing, the system controller 12 judges in Step S8 whether or not the voice command uttered by the operator is recognized as the second hierarchical language. When the voice command is recognized as the second hierarchical language, the system controller 12 executes a command recognized from the first hierarchical language and the second hierarchical language in Step S9.

Then, the system controller 12 causes the voice synthesizing engine 113 to utter a second hierarchical guidance corresponding to the second hierarchical language from the speaker 32 after a predetermined interval time period (for example, three seconds) in Step S10, to terminate the processing.

When judging the voice command cannot be recognized in Step S2 and Step S8, the system controller 12 performs error determination (Steps S11, S13) to allow error guidance to be uttered from the speaker 32 (Steps S12, S14).

Thus, in the present embodiment, when the voice command uttered by the operator is recognized as the first hierarchical language, the system controller 12 allows the first hierarchical guidance corresponding to the first hierarchical language to be outputted from the speaker 32 and urges the operator to utter the second hierarchical language.

When recognizing the voice command uttered by the operator in response to the first hierarchical guidance as the second hierarchical language, the system controller 12 allows the second hierarchical guidance corresponding to the second hierarchical language to be outputted from the speaker 32.

In addition, when recognizing both of the first hierarchical language and the second hierarchical language, the system controller 12 determines one command.

For example, when recognizing the first hierarchical language, "gas insufflator insufflation" and the second hierarchical language, "start", the system controller 12 determines the command "start gas insufflator insufflation".

Utterance timings of response guidances which are the first hierarchical guidance in response to each language of the first hierarchical language and the second hierarchical guidance in response to the second hierarchical language will be specifically shown in FIGS. 9 to 23. The utterance timings of the response guidances are briefly described taking FIG. 9 as an example.

Figure 9:
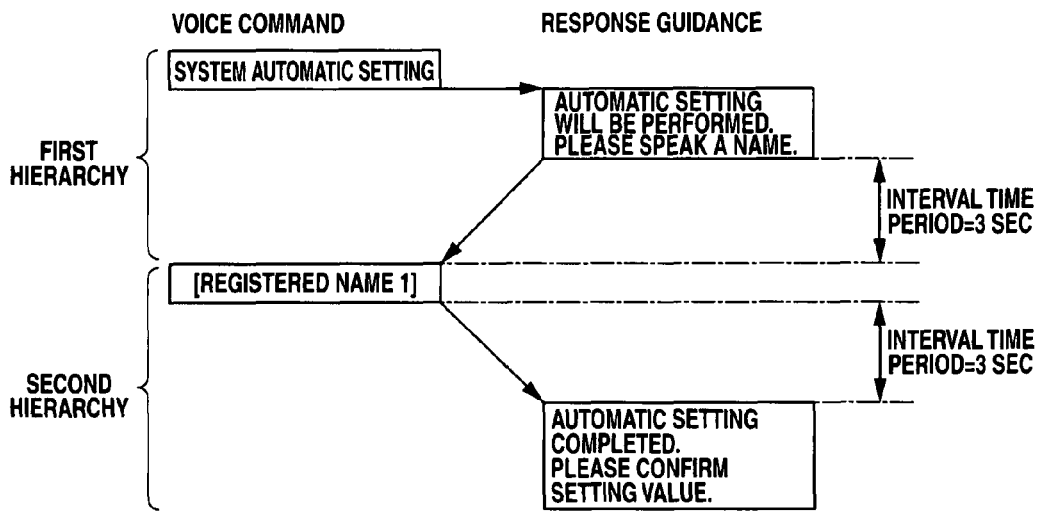
Figure 10:
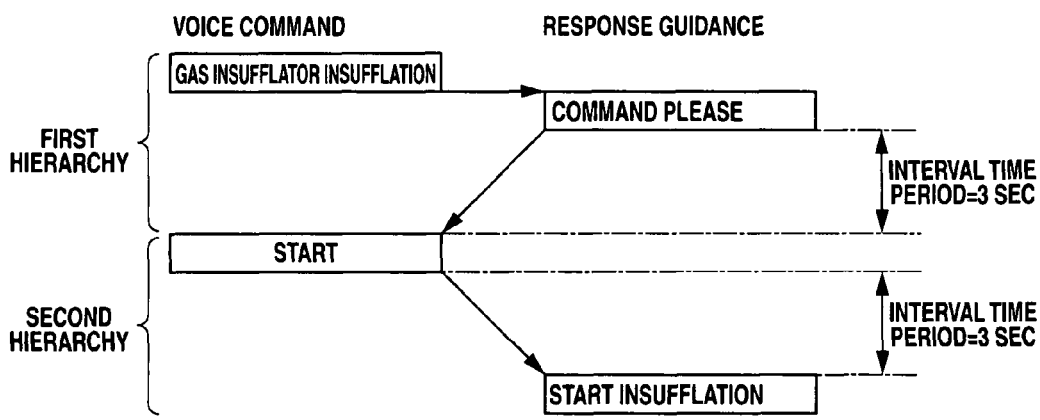
Figure 11:
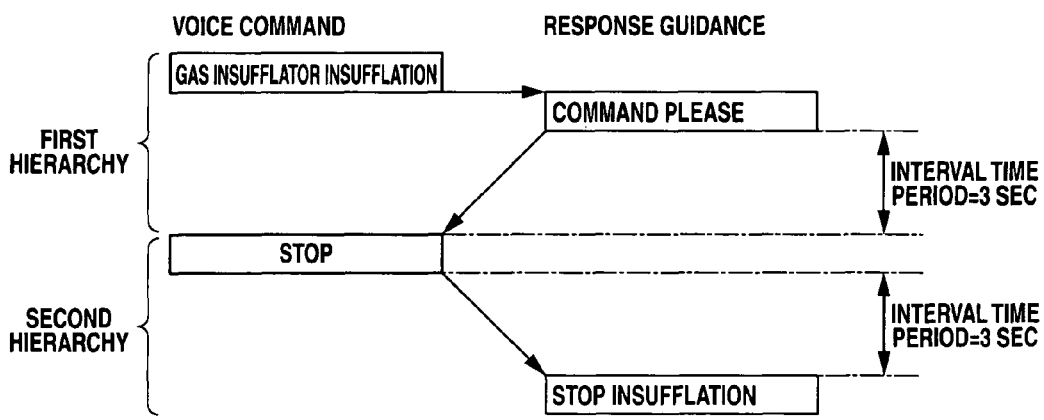
Figure 12:
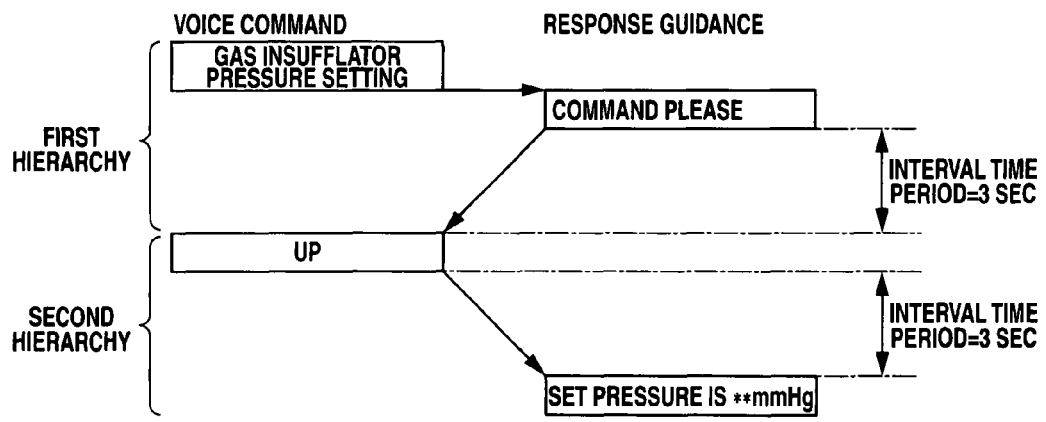
Figure 13:
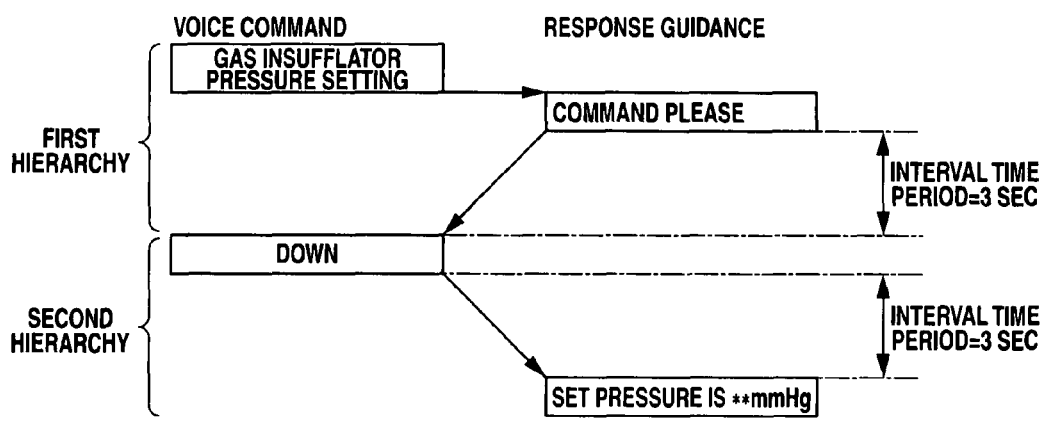
Figure 14:
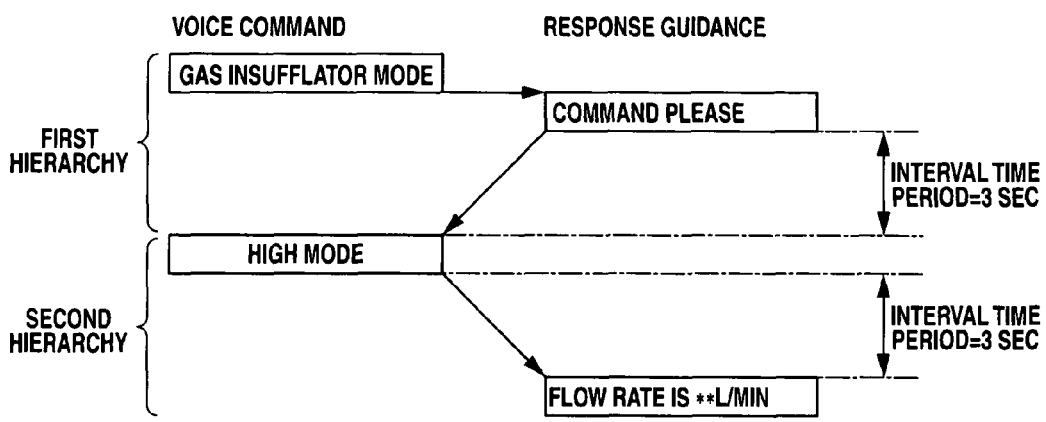
Figure 15:
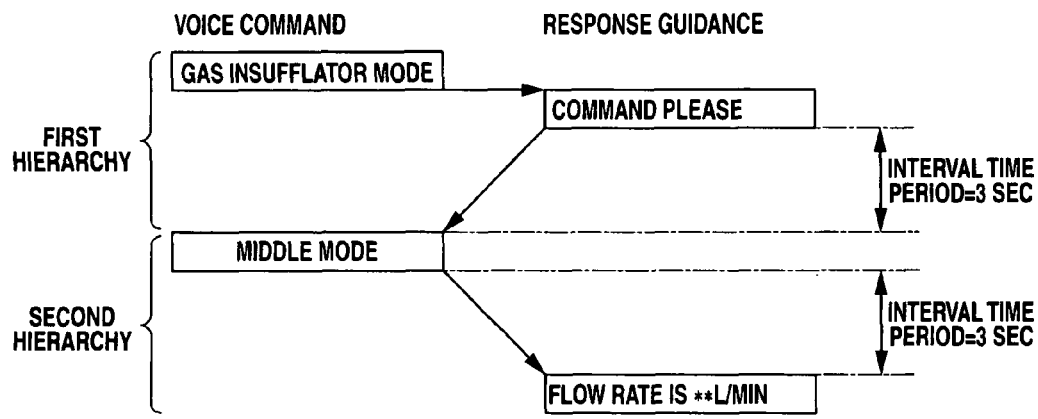
Figure 16:
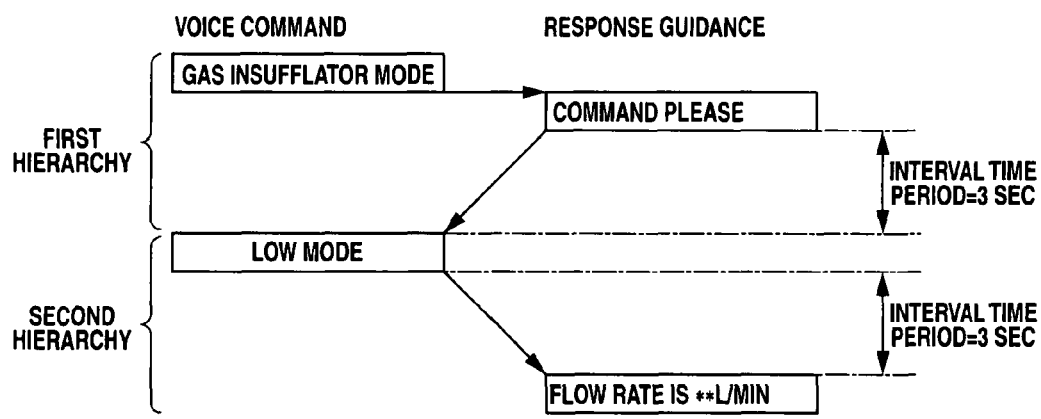
Figure 17:
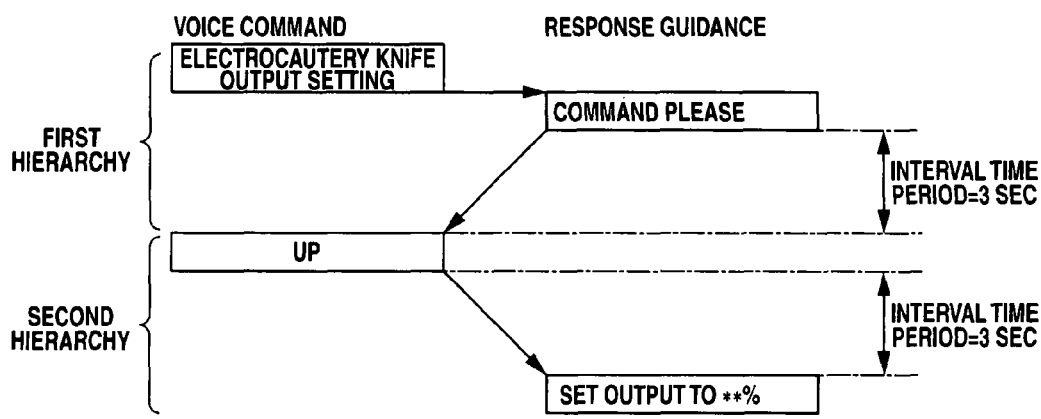
Figure 18:
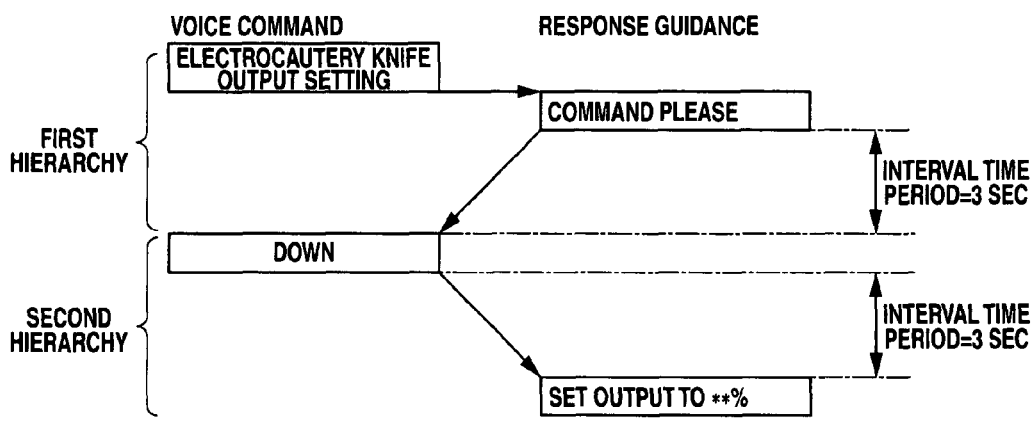
Figure 19:
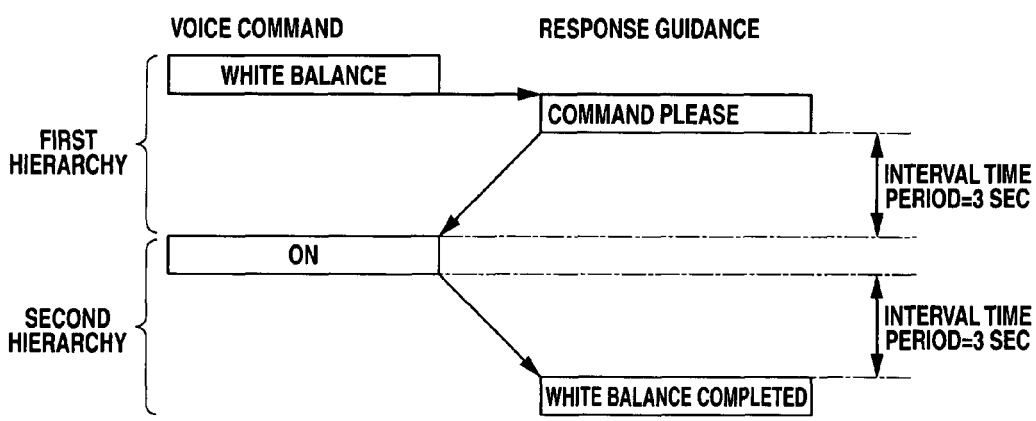
Figure 20:
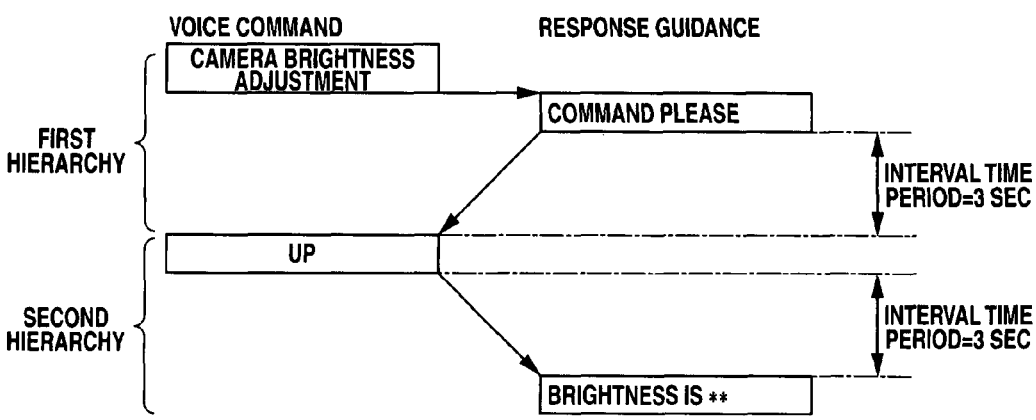
Figure 21:
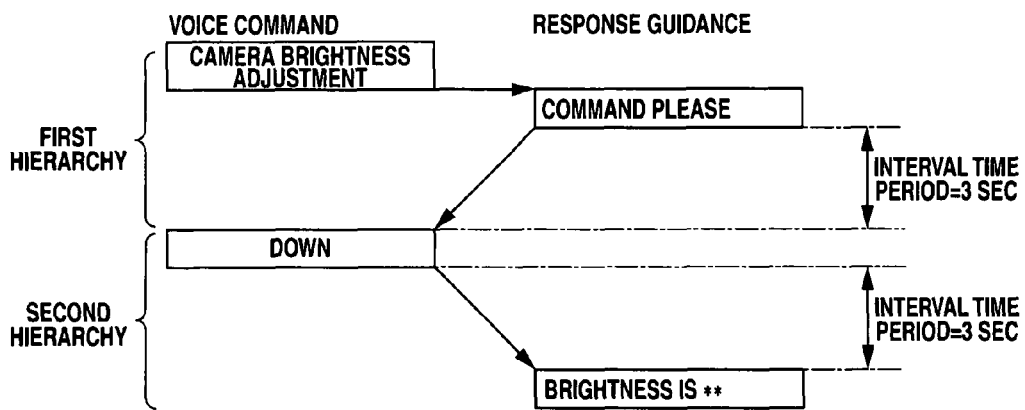
Figure 22:
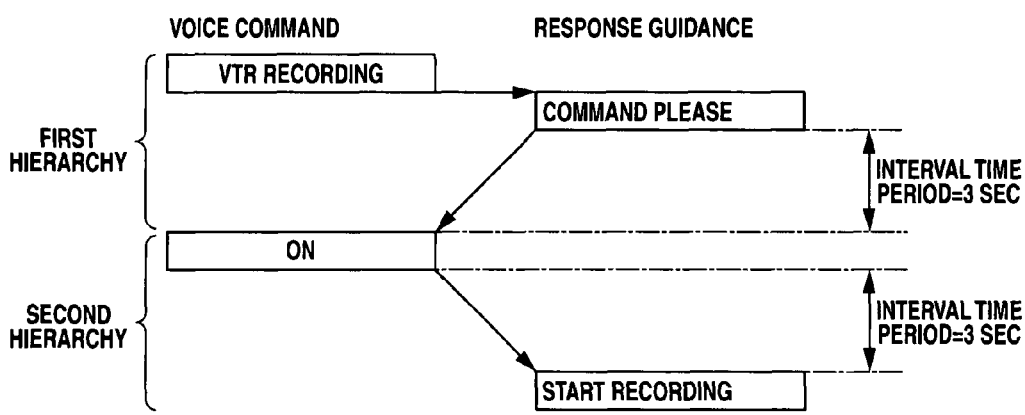
Figure 23:
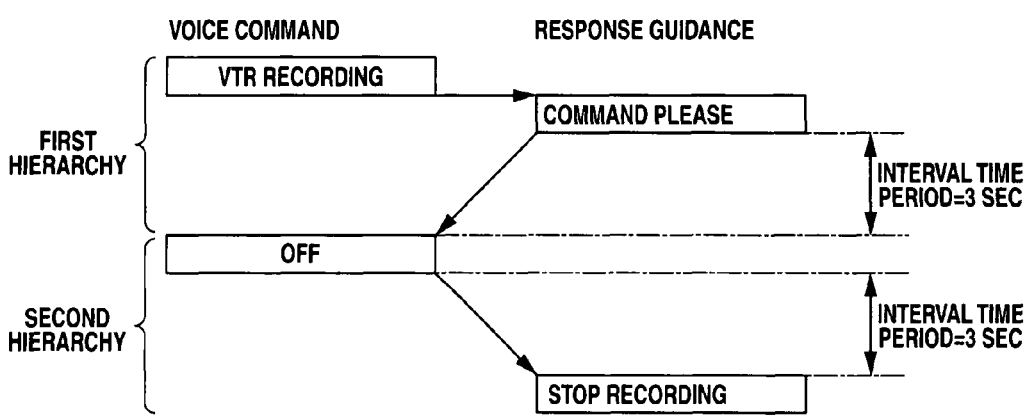

As shown in FIG. 9, when recognizing the voice command uttered by the operator is "system automatic setting" of the first hierarchical language, the system controller 12 allows the response guidance, for example, "Automatically setting will be performed, please speak a name" to be outputted from the speaker 32 as the first hierarchical guidance.

The operator is urged by the response guidance as the first hierarchical guidance to utter the corresponding second hierarchical language, that is, the registered operator's name "[registered name 1](="Dr. TANAKA" and the like) within a predetermined interval time period (for example, three seconds), and thereby the system controller 12 recognizes the "[registered name 1]" of the second hierarchical language.

Then, the system controller 12 executes the command "system automatic setting: [registered name 1]" based on the first hierarchical language and the second hierarchical language. After that, the system controller 12 performs setting with respect to the group of medical instruments in accordance with the registered operator [registered name 1], and after the predetermined interval time period (for example, three seconds), outputs the response guidance, for example, "Automatic setting completed. Please confirm the setting value." as the second hierarchical guidance from the speaker 32.

Next, the voice recognition processings in the above-described Steps S1 and S7 will be described using the flowcharts in FIGS. 24 and 25.

Figure 24:
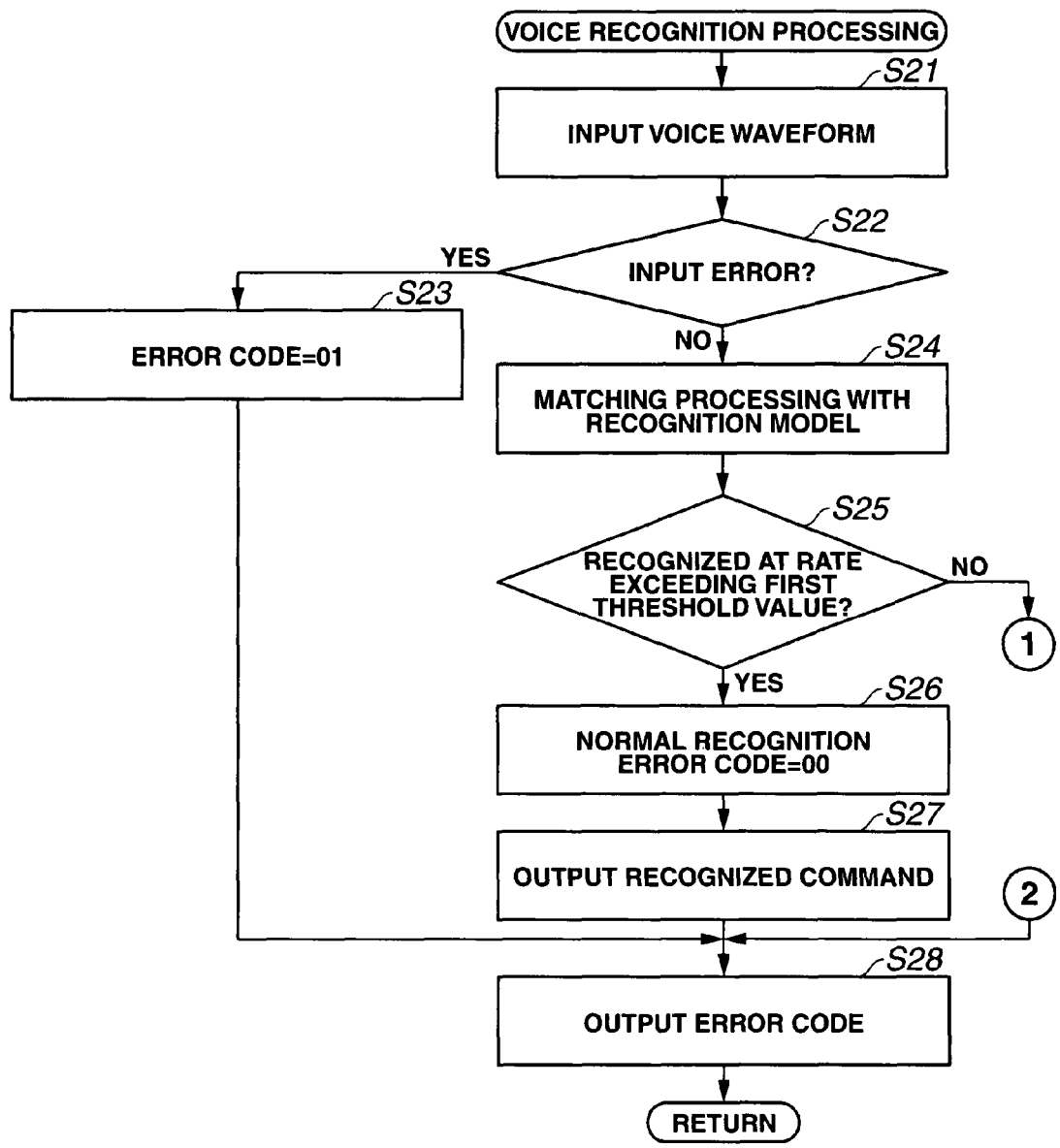

As shown in FIG. 24, in the voice recognition processing, the voice recognition engine 110 is inputted in Step S21 with the voice waveform of the inputted voice input signal, and judges in Step S22 whether or not the level of the voice input signal is lower than a predetermined voice level, that is, an input error.

The voice recognition engine 110, when the input is an error, sets an error code to 01 (error code=01) in Step 23 to proceed to Step S28.

The voice recognition engine 110, when the input is not an error, that is, the level of the voice input signal is equal to or higher than a predetermined voice level, performs a matching processing between the recognition model 111 including vowels and consonants and the voice waveform of the voice input signal in Step S24.

Then, the voice recognition engine 110 judges in Step S25 whether or not the voice input signal can be recognized at a rate exceeding a first threshold value (for example, matching rate is equal to 80%) of the matching rate set in the matching rate setting section 106. Subsequently, the voice recognition engine 110, if the voice input signal can be recognized at a rate exceeding the first threshold value, sets the error code to 00 (error code=00) as normal recognition in Step S26, and outputs the error code to the controlling section 103 to terminate the processing.

Figure 26:
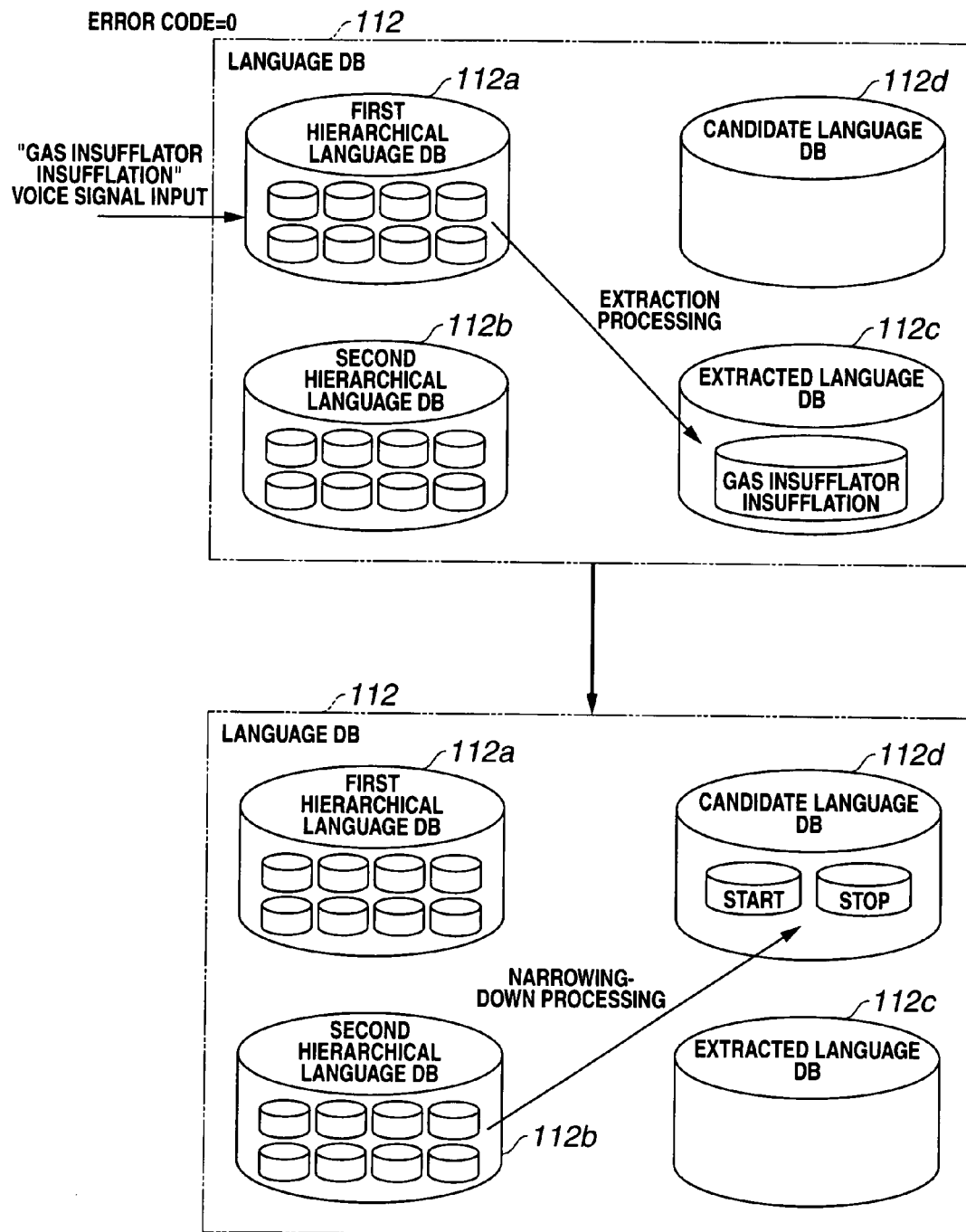

If the error code is 00 in the recognition of the first hierarchical language, in the language DB 112, the corresponding language "gas insufflator insufflation", for example, is extracted from the first hierarchical language DB 112a to be stored in the extracted language DB 112c, as shown in FIG. 26. Then, the voice recognition engine 110 outputs the extracted language and error code which is 00 to the controlling section 103 and stores them in the data management section 104. When the extraction of the first hierarchical language is finished, the voice recognition engine 110 stores the languages of the second hierarchical language, "Start", "Stop", for example, associated with the extracted language of the first hierarchical language, in the candidate language DB 112*d* as the candidate language.

Figure 25:
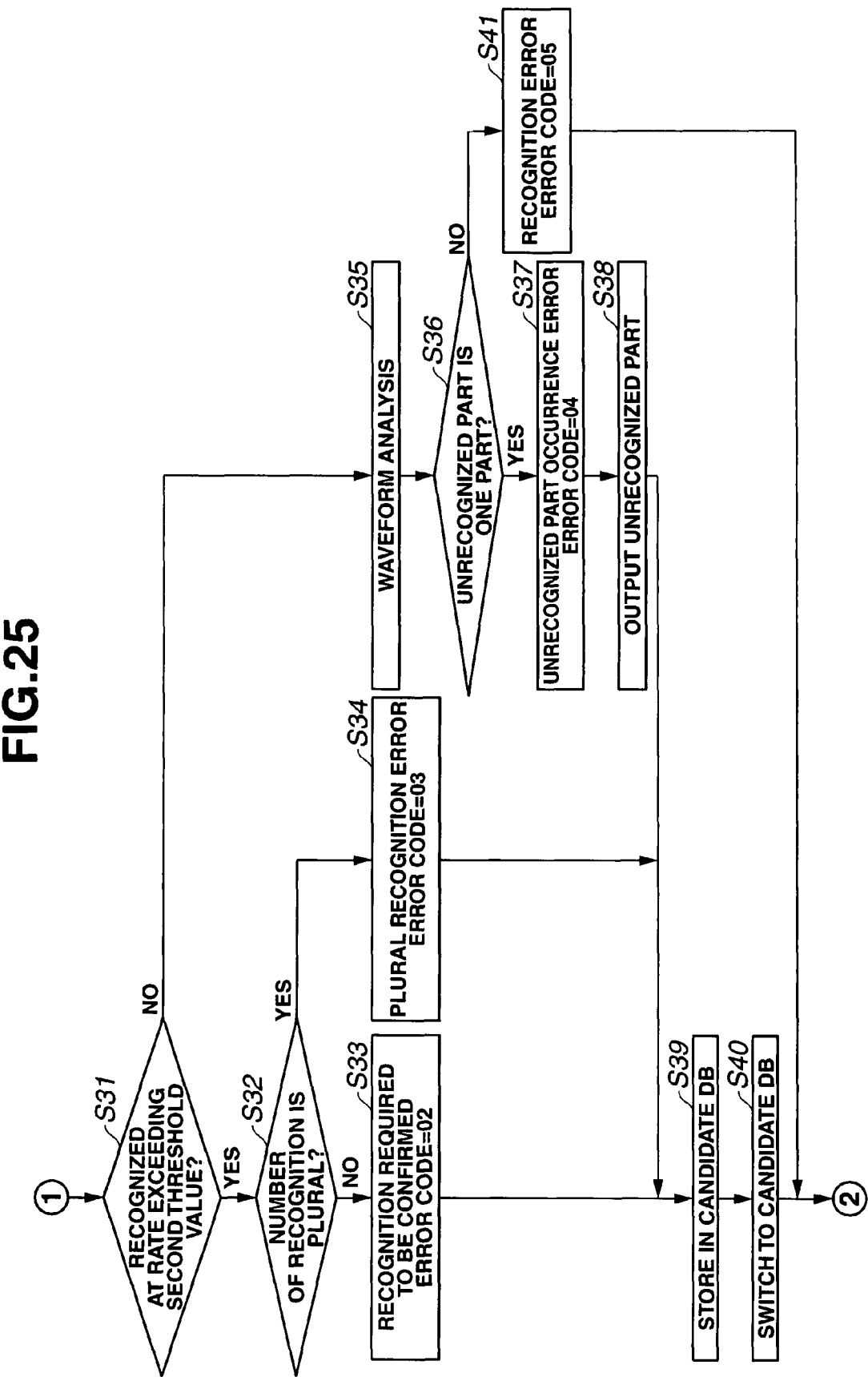

When judging that the voice input signal is not recognized at a rate exceeding the first threshold value in Step S25, the voice recognition engine 110 transfers to Step S31 in FIG. 25, and judges in Step S31 whether or not the voice input signal can be recognized at a rate equal to or higher than a second threshold value (for example, the matching rate is equal to 60%) of the matching rate set in the matching rate setting section 106.

If the voice input signal is recognized at a rate equal to or higher than the second threshold value, it means that the voice input signal is recognized at an uncertain matching rate from equal to or higher than 60% to equal to or lower than 80%. Accordingly, there is a case where the first hierarchical language is not uniquely determined in the recognition, so that the voice recognition engine 110 judges whether or not the number of recognition is plural in Step S32.

When the number of recognition is one, the voice recognition engine 110 sets the error code to 02 (error code=02) in Step S33 as a recognition required to be confirmed error, and then proceeds to Step S39.

Figure 27:
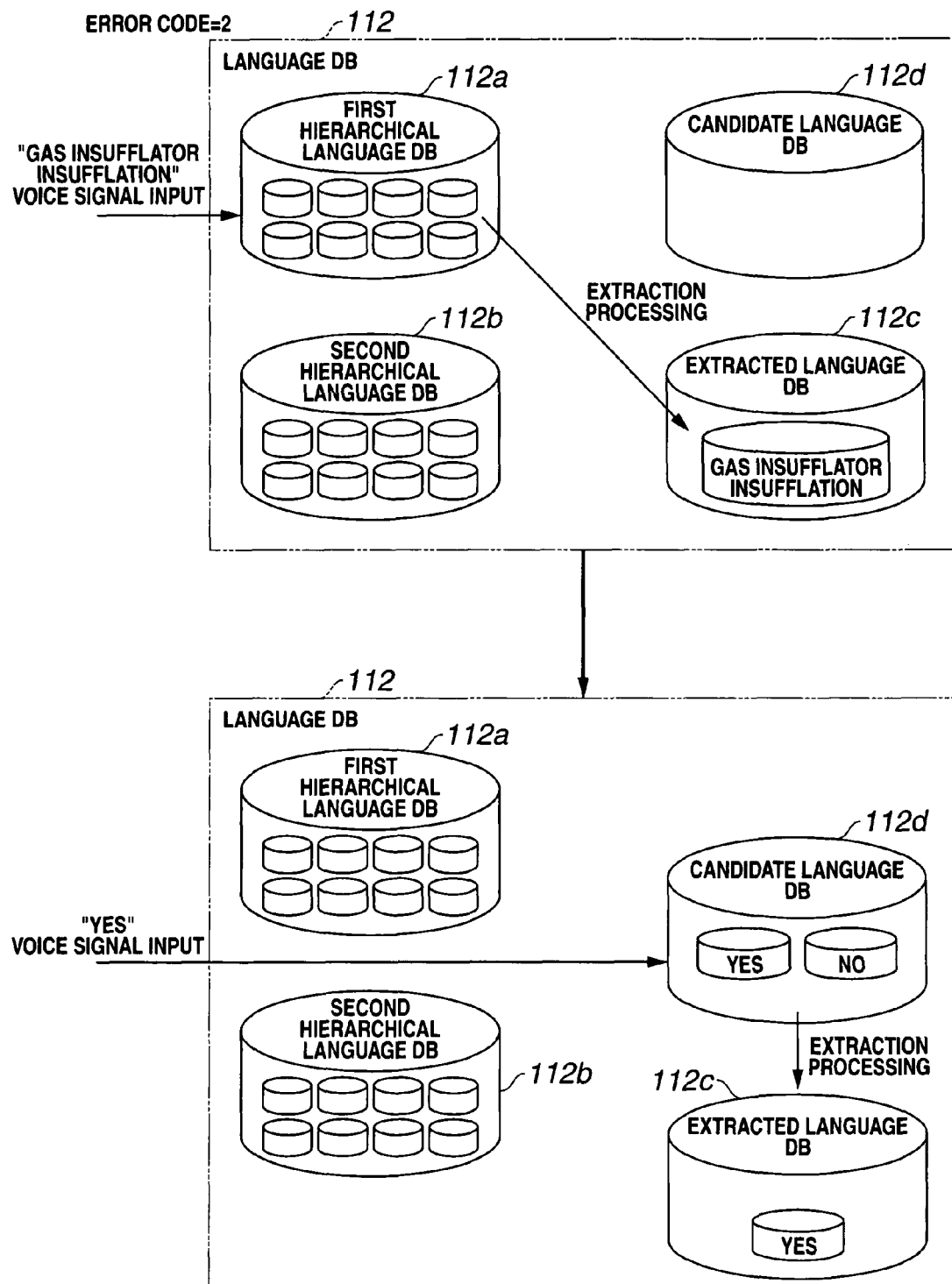

In this case, in the language DB 112, the language, "gas insufflator insufflation", for example, corresponding to the voice input signal recognized at an uncertain matching rate is extracted from the first hierarchical language DB 112*a* to be stored in the extracted language DB 112*c*, as shown in FIG. 27. Then, the voice recognition engine 110 outputs the extracted language and the error code which is 02 to the controlling section 103 to store them in the data management section 104.

When the extraction of the first hierarchical language recognized at the uncertain matching rate is finished, the voice recognition engine 110 stores, from the second hierarchical language DB 112*b*, confirmation language "Yes", "No", for example, for confirming the extracted language of the first hierarchical language, in the candidate language DB 112*d* as candidate language in Step S39, thereafter proceeding to Step S40.

In the case where the error code is 02, the controlling section 103 urges the operator from the speaker 32 to utter the confirmation language, and the first hierarchical language is confirmed based on the confirmation language.

On the other hand, when it is judged that the number of recognition is plural in Step S32, the voice recognition engine 110 sets the error code to 03 (error code=03) as plural recognition error in Step S34 to proceed to Step S39.

Figure 28:
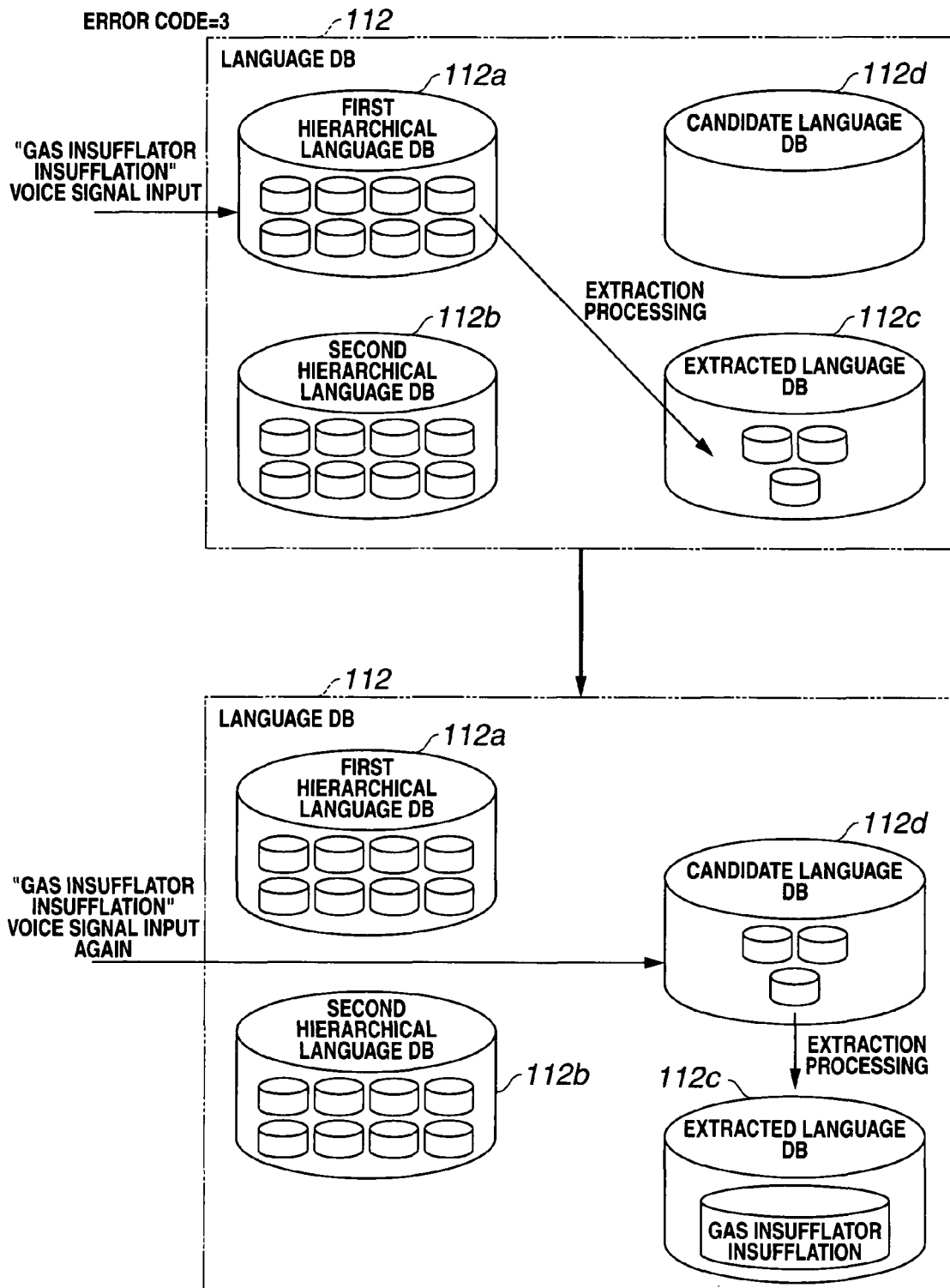

In this case, as shown in FIG. 28, in the language DB 112, a plurality of, for example, three languages, for example, "gas insufflator insufflation", "gas insufflator pressure setting", and "gas insufflator mode" which are recognized at an uncertain matching rate are extracted as the first hierarchical language, to be stored in the extracted language DB 112*c*. At this time, the voice recognition engine 110 outputs the extracted language and the error code which is 03 to the controlling section 103 and store them in the data management section 104.

When the extraction of the first hierarchical language recognized at the uncertain matching rate is finished, the voice recognition engine 110 reads out the three languages "gas insufflator insufflation", "gas insufflator pressure setting", and "gas insufflator mode" as the first hierarchical language recognized at the uncertain matching rate from the second hierarchical language DB 112*b* and stores the three languages as the candidate languages in the candidate language DB 112*d* to proceed to the Step S40.

In the case where the error code is 03, the controlling section 103 urges the operator from the speaker 32 to utter the command again, and the first hierarchical language is extracted based on the language uttered again.

In addition, if it is judged that the voice input signal is incognizable at the rate equal to or higher than the second threshold value, the voice recognition engine 110 analyzes the voice waveform in Step S35, to judge whether or not the unrecognized part is one part of the voice input signal in Step S36.

If it is judged that the unrecognized part is one part of the voice input signal, the voice recognition engine 110 sets the error code to 04 (error code=04) as an unrecognized part occurrence error in Step S37, to output the unrecognized part to the controlling section 103 in Step S38, thereafter proceeding to Step S39.

Figure 29:
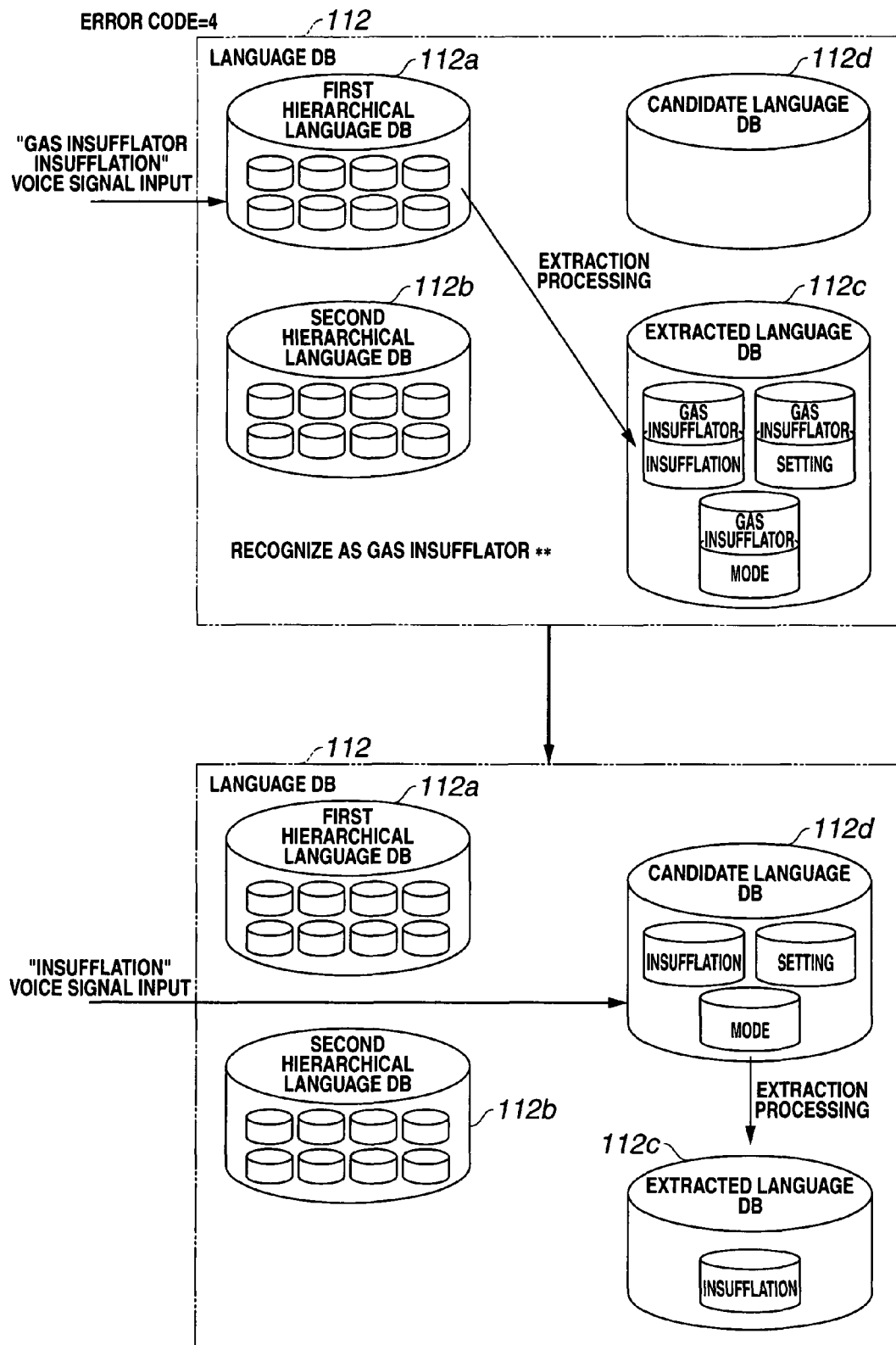

In this case, in the language DB 112, as shown in FIG. 29, if "gas insufflator @@" (the part @@ is unrecognized part) is extracted, for example, as the first hierarchical language including the unrecognized part, the three languages "gas insufflator insufflation", "gas insufflator pressure setting", and "gas insufflator mode" are extracted with the unrecognized part ignored.

Accordingly, the voice recognition engine 110 recognizes the "gas insufflator @@" as a hierarchical language composed of "gas insufflator" and "@@".

That is, the voice recognition engine 110 separates the languages as the hierarchical languages, such as ["gas insufflator insufflation"="gas insufflator"+"insufflation"], ["gas insufflator pressure setting"="gas insufflator"+"pressure setting"], and ["gas insufflator mode"="gas insufflator"+ "mode"]. Then, the voice recognition engine 110 stores in the extracted language DB 112*c* the "insufflation", "pressure setting", and "mode" which fall under the unrecognized part "@@". After that, the voice recognition engine 110 outputs the unrecognized part languages and the error code which is 04 to the controlling section 103 to store them in the data management section 104.

Then, when the extraction of the first hierarchical language recognized at the uncertain matching rate is finished, the voice recognition engine 110 stores the three languages "insufflation", "pressure setting", and "mode" as the first hierarchical language recognized at the uncertain matching rate in the candidate language DB 112*d* as the candidate language in Step S39, and thereafter proceeds to Step S40.

In the case where the error code is 04, the controlling section 103 urges the operator from the speaker 32 to utter the unrecognized-part language, and the first hierarchical language is extracted based on the uttered unrecognized-part language.

When judging that the unrecognized part of the voice input signal is not a part of the signal but whole of the signal in Step S36, the voice recognition engine 110 sets the error code to 05 (error code =05) as recognition error in Step S41, thereafter returning to Step S28 in FIG. 24.

Then, the voice recognition engine 110 switches the target database for voice recognition processing to the extracted language DB 112*c* in Step S40 to return to Step S28 in FIG. 24.

Figure 30:
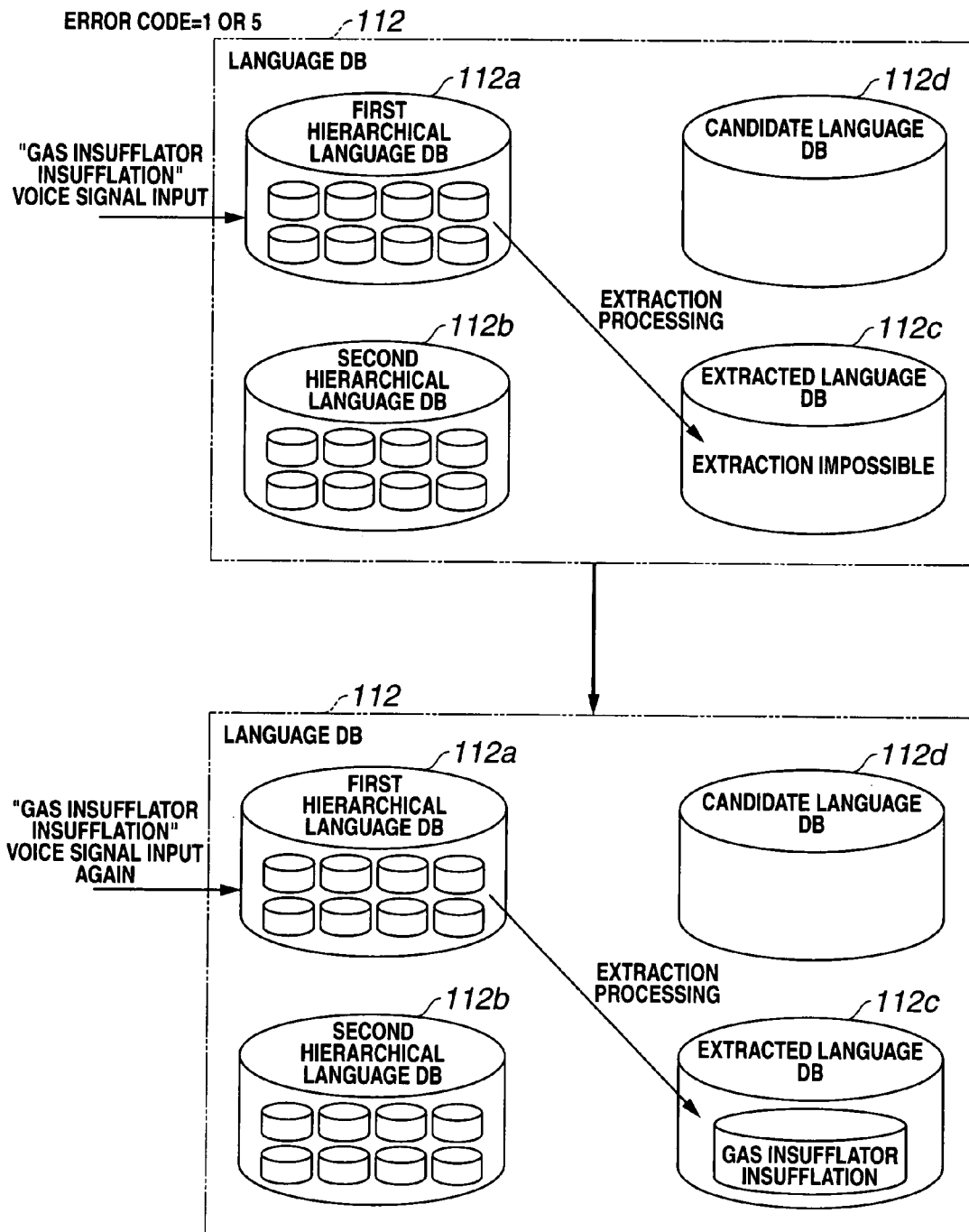

Note that, in the above described cases where the error code is 01 or 05, it is not possible to extract the target language as shown in FIG. 30, since the voice input signal is incognizable. Therefore, the controlling section 103 again urges the operator from the speaker 32 to utter the command, and the first hierarchical language is extracted based on the command uttered again.

In addition, the controlling section 103, in the above-described error codes, executes the error guidance including guidance as to causes of error and guidance as to contents to be improved in Steps S12 and S14 in FIG. 8 from the speaker 32 to the operator.

Though the command generating processing with respect to the group of medical instruments by means of utterance of the operator has been described above, events such as command generation with respect to the group of medical instruments occur not only by the utterance of the operator but also by the operation of each apparatus of the group of medical instruments and update of status (measurement value of abdominal cavity pressure, alarm information, and the like) displayed on the centralized operation panel 11. In the present embodiment, an appropriate guidance with respect to such an event occurrence is provided from the speaker 32.

Figure 32:
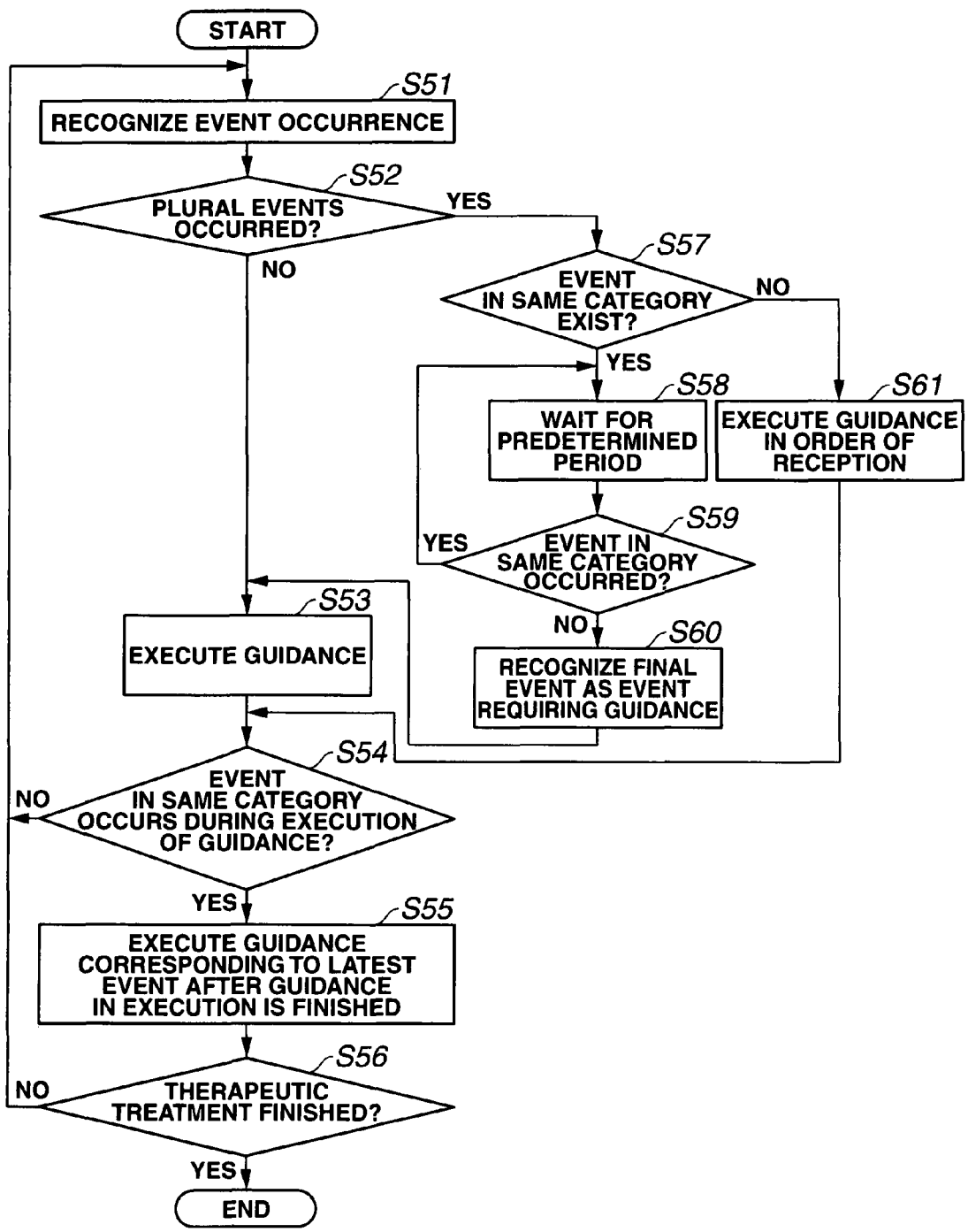

Specifically, when recognizing occurrence of an event in Step S51, the system controller 12 judges in Step S52 whether or not a plurality of events have occurred, as shown in FIG. 32.

In a case where the number of occurred event is one, the system controller 12 provides guidance in accordance with the event from the speaker 32, to proceed to Step S54.

In Step S54, the system controller 12 judges whether or not an event of the same category has occurred during execution of guidance. If the event in the same category has not occurred, the processing returns to Step S51. If the event in the same category has occurred, the processing proceeds to Step S55.

Here, taking the gas insufflator as an example, the occurrence of the event in the same category means that "gas insufflator insufflation stop" in the category of the gas insufflator insufflation occurs during the execution of guidance corresponding to "start gas insufflator insufflation".

Then, in Step S55, the system controller 12, after the guidance currently being executed is finished, provides from the speaker 32 the guidance corresponding to the latest event, and repeats the processings from Step S51 to Step 56 until the therapeutic procedure is terminated in Step S56.

Figure 33:
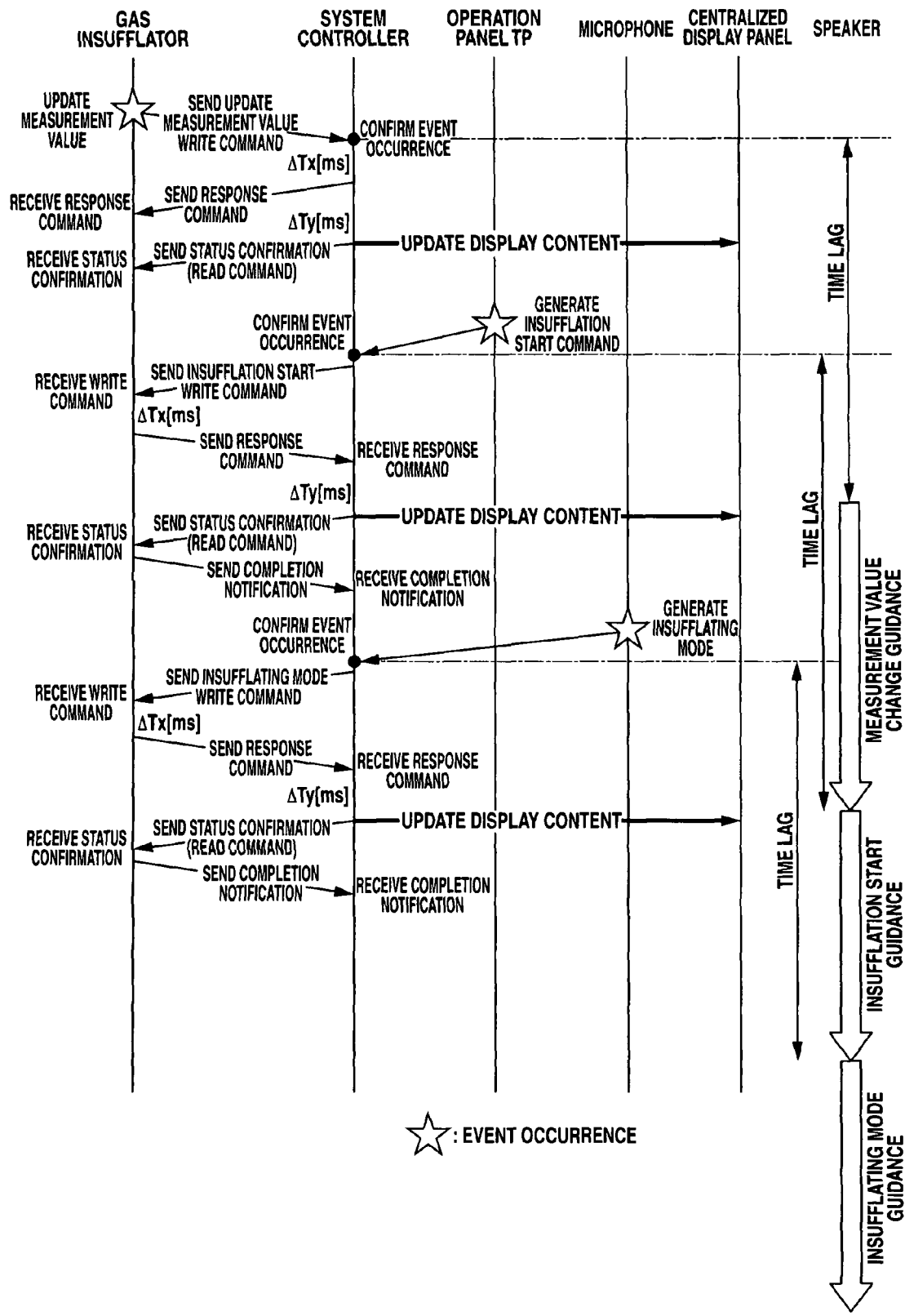
Figure 34:
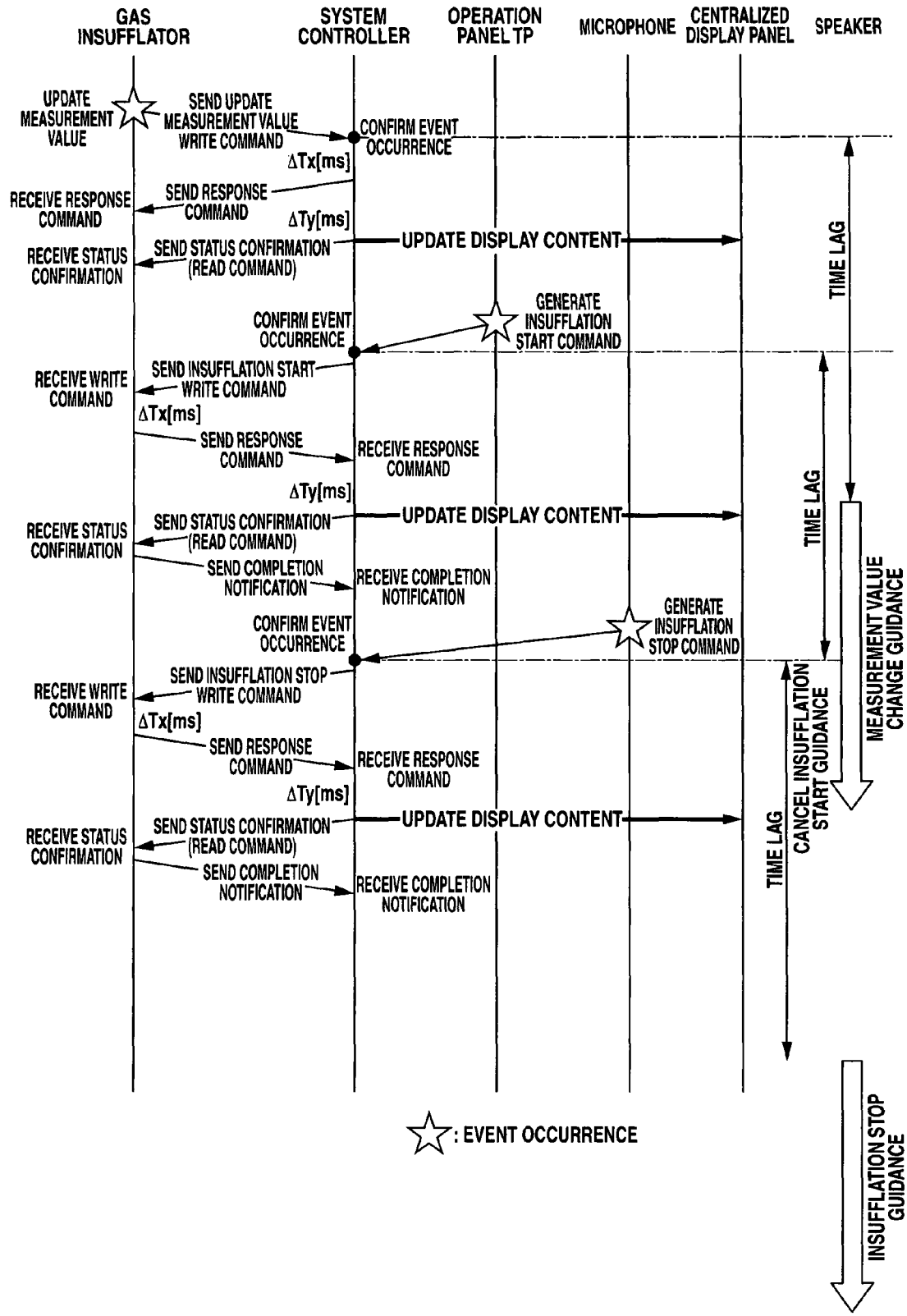

FIG. 33 shows a transition of control state of the system controller in a case where the number of occurred event is one and no event in the same category occurs during the execution of the guidance. FIG. 34 shows a transition of control state of the system controller in a case where the number of occurred event is one and the event in the same category occurs during the execution of the guidance.

On the other hand, when judging that a plurality of events occur in Step S52, the system controller 12 judges in Step S57 whether or not an event in the same category exists in the plurality of events.

When the event in the same category exists, the system controller 12 waits in Steps S58 and S59 whether or not another event in the same category occurs in a predetermined period, and recognizes the final event as the event to which guidance is to be provided, thereafter proceeding to Step S53.

Furthermore, when judging that no event in the same category exists in Step S57, the system controller 12 provides the guidance corresponding to the event in an order of occurrence, to proceed to Step S54. FIG. 35 shows an example of guidance in response to the occurred event.

As described above, with the present embodiment, when the voice command uttered by the operator is recognized as the first hierarchical language, the first hierarchical guidance corresponding to the first hierarchical language is outputted, thereby urging the operator to utter the second hierarchical language. When the voice command uttered by the operator in response to the first hierarchical guidance is recognized as the second hierarchical language, the second hierarchical guidance corresponding to the second hierarchical language is outputted. When both the first hierarchical language and the second hierarchical language are recognized, one command is determined, so that operatability by voice operation can be improved, while reducing a risk of misrecognition by maintaining a predetermined matching rate.

It should be understood that the present invention is not limited to those precise embodiments and various changes and modifications thereof could be made by one skilled in the art without departing from the spirit or scope of the invention as defined in the appended claims.

What is claimed is:

1. A surgical system controlling apparatus, comprising:
a voice information inputting section for inputting operation state voice information related to an operation state of a surgical instrument to be controlled;
a voice recognition processing section for recognizing the operation state voice information based on operation state standard voice data;
a guidance data storing section for storing at least guidance data according to a recognition state in the voice recognition processing section; and
a guidance voice generating section for generating voice data based on the guidance data,
wherein, when a matching rate of either first operation state voice information or second operation state voice information with respect to the operation state standard voice data is equal to or lower than a predetermined first value, the voice recognition processing section judges that the operation state voice information cannot be hierarchically recognized; and
when the voice recognition processing section judges that the operation state voice information cannot be hierarchically recognized, the guidance voice generating section generates voice data based on guidance as to causes of error and guidance as to contents to be improved which are stored in the guidance data storing section and allows the generated voice data to be outputted.

2. The surgical system controlling apparatus according to claim 1, wherein the recognition state is classified by a code based on a matching result in the voice recognition processing section.

3. The surgical system controlling apparatus according to claim 2, further comprising an operation information inputting section for inputting operation information related to an operation state of the surgical instrument to be controlled, wherein the guidance voice generating section generates voice data based on the guidance data according to a change of the operation state voice information and/or the operation information.

4. The surgical system controlling apparatus according to claim 1, wherein the recognition state is classified by a code based on a matching result in the voice recognition processing section.

5. The surgical system controlling apparatus according to claim 4, further comprising an operation information inputting section for inputting operation information related to an operation state of the surgical instrument to be controlled, wherein the guidance voice generating section generates voice data based on the guidance data according to a change of the operation state voice information and/or the operation information.

6. The surgical system controlling apparatus according to claim 1, further comprising an operation information inputting section for inputting operation information related to an operation state of the surgical instrument to be controlled, wherein the guidance voice generating section generates voice data based on the guidance data according to a change of the operation state voice information and/or the operation information.

7. The surgical system controlling apparatus according to claim 1, further comprising an operation information inputting section for inputting operation information related to an operation state of the surgical instrument to be controlled, wherein the guidance voice generating section generates voice data based on the guidance data according to a change of the operation state voice information and/or the operation information.

8. The surgical system controlling apparatus according to claim 1, wherein, when the matching rate of either the first operation state voice information or the second operation state voice information with respect to the operation state standard voice data is equal to or lower than the predetermined first value and equal to or higher than a predetermined second value which is lower than the predetermined first value, the voice recognition processing section further judges whether or not languages extracted from languages in the guidance data according to the matching rate are narrowed down to one language.

9. The surgical system controlling apparatus according to claim 8, wherein, when the voice recognition processing section judges that the languages extracted from the languages in the guidance data are narrowed down to one language, the guidance voice generating section generates voice data for confirming the one language and allows the generated voice data to be outputted.

10. The surgical system controlling apparatus according to claim 8, wherein, when the voice recognition processing section judges that the languages extracted from the languages in the guidance data are not narrowed down to one language, the guidance voice generating section generates voice data for urging reinput of the first operation state voice information or the second operation state voice information according to the judgment result and allows the generated voice data to be outputted.

11. The surgical system controlling apparatus according to claim 1, wherein, when the matching rate of either the first operation state voice information or the second operation state voice information with respect to the operation state standard voice data is equal to or lower than the predetermined first value and lower than a predetermined second value which is lower than the predetermined first value, the voice recognition processing section further judges that either a part of or a whole of the operation state voice information inputted from the voice information inputting section is an unrecognized part.

12. The surgical system controlling apparatus to claim 11, wherein, when the voice recognition processing section judges that a part of the operation state voice information is the unrecognized part, the guidance voice generating section generates voice data for confirming the unrecognized part and allows the generated voice data to be outputted.

13. The surgical system controlling apparatus according to claim 11, wherein, when the voice recognition processing section judges that the whole of the operation state voice information is the unrecognized part, the guidance voice generating section generates voice data for urging reinput of the first operation state voice information or the second operation state voice information according to the judgment result and allows the generated voice data to be outputted.

14. The surgical system controlling apparatus according to claim 1, wherein, when matching rates of the first operation state voice information and the second operation state voice information with respect to the operation state standard voice data exceed the predetermined first value, the voice recognition processing section judges that the operation state voice information can be hierarchically recognized, and when the voice recognition processing section judges that the operation state voice information can be hierarchically recognized, the guidance voice generating section generates voice data for the first operation state voice information and allows the generated voice data to be outputted, and thereafter generates voice data for the second operation state voice information and allows the generated voice data to be outputted.

15. A surgical system controlling method, comprising:
a voice information inputting step in which operation state voice information related to an operation state of a surgical instrument to be controlled is inputted;
a voice recognition processing step in which the operation state voice information is recognized based on operation state standard voice data;
a guidance data storing step in which at least guidance data according to a recognition state in the voice recognition processing step is stored; and
a guidance voice generating step in which voice data based on the guidance data is generated,
wherein, when a matching rate of either first operation state voice information or second operation state voice information with respect to the operation state standard voice data is equal to or lower than a predetermined first value, it is judged that the operation state voice information including the first operation state voice information and the second operation state voice information cannot be hierarchically recognized in the voice recognition processing step, and
when it is judged that the operation state voice information cannot be hierarchically recognized in the voice recognition processing step, voice data based on guidance as to causes of error and guidance as to contents to be improved which are stored in the guidance data storing step is generated and allowed to be outputted in the guidance voice generating step.

16. The surgical system controlling method according to claim 15, wherein the recognition state is classified by a code based on a matching result in the voice recognition processing step.

17. The surgical system controlling method according to claim 16, further comprising an operation information inputting step in which operation information related to an operation state of the surgical instrument to be controlled is inputted, wherein voice data based on the guidance data according to a change of the operation state voice information and/or the operation information is generated in the guidance voice generating step.

18. The surgical system controlling method according to claim 15, wherein the recognition state is classified by a code based on a matching result in the voice recognition processing step.

19. The surgical system controlling method according to claim 18, further comprising an operation information inputting step in which operation information related to an operation state of the surgical instrument to be controlled is inputted, wherein voice data based on the guidance data according to a change of the operation state voice information and/or the operation information is generated in the guidance voice generating step.

20. The surgical system controlling method according to claim 15, further comprising an operation information inputting step in which operation information related to an operation state of the surgical instrument to be controlled is inputted, wherein voice data based on the guidance data according to a change of the operation state voice information and/or the operation information is generated in the guidance voice generating step.

21. The surgical system controlling method according to claim 15, further comprising an operation information inputting step in which operation information related to an operation state of the surgical instrument to be controlled is inputted, wherein voice data based on the guidance data according to a change of the operation state voice information and/or the operation information is generated in the guidance voice generating step.

22. The surgical system controlling method according to claim 15, wherein, when the matching rate of either the first operation state voice information or the second operation state voice information with respect to the operation state standard voice data is equal to or lower than the predetermined first value and equal to or higher than a predetermined second value which is lower than the predetermined first value, it is further judged whether or not languages extracted from languages in the guidance data according to the matching rate are narrowed down to one language in the voice recognition processing step.

23. The surgical system controlling method according to claim 22, wherein, when it is judged that the languages extracted from the languages in the guidance data are narrowed down to one language in the voice recognition processing step, voice data for confirming the one language is generated and allowed to be outputted in the guidance voice generating step.

24. The surgical system controlling method according to claim 22, wherein, when it is judged that the languages extracted from the languages in the guidance data are not narrowed down to one language in the voice recognition processing step, voice data for urging reinput of the first operation state voice information or the second operation state voice information according to the judgment result is generated and allowed to be outputted in the guidance voice generating step.

25. The surgical system controlling method according to claim 15, wherein, when the matching rate of either the first operation state voice information or the second operation state voice information with respect to the operation state standard voice data is equal to or lower than the predetermined first value and lower than a predetermined second value which is lower than the predetermined first value, it is further judged that either a part of or a whole of the operation state voice information inputted in the voice information inputting step is an unrecognized part in the voice recognition processing step.

26. The surgical system controlling method according to claim 25, wherein, when it is judged that a part of the operations state voice information is the unrecognized part in the voice recognition processing step, voice data for confirming the unrecognized part is generated and allowed to be outputted in the guidance voice generating step.

27. The surgical system controlling method according to claim 25, wherein, when it is judged that the whole of the operation state voice information is the unrecognized part in the voice recognition processing step, voice data for urging reinput of the first operation state voice information or the second operation state voice information according to the judgment result is generated and allowed to be outputted in the guidance voice generating step.

28. The surgical system controlling method according to claim 15, wherein, when matching rates of the first operation state voice information and the second operation state voice information with respect to the operation state standard voice data exceed the predetermined first value, it is judged that the operation state voice information can be hierarchically recognized in the voice recognition processing step, and when it is judged that the operation state voice information can be hierarchically recognized in the voice recognition processing step, voice data for the first operation state voice information is generated and allowed to be outputted, and thereafter voice data for the second operation state voice information is generated and allowed to be outputted in the guidance voice generating step.

* * * * *